US012577469B2

(12) United States Patent
Okubo et al.

(10) Patent No.: US 12,577,469 B2
(45) **Date of Patent: *Mar. 17, 2026**

(54) COMPOUND, COMPOSITION, CURED PRODUCT, OPTICALLY ANISOTROPIC BODY, OPTICAL ELEMENT, AND LIGHT GUIDE ELEMENT

(71) Applicant: FUJIFILM Corporation, Tokyo (JP)

(72) Inventors: Megumi Okubo, Minami-Ashigara (JP); Yuki Fukushima, Minami-Ashigara (JP); Keisuke Kodama, Minami-Ashigara (JP); Shunya Katoh, Minami-Ashigara (JP)

(73) Assignee: FUJIFILM Corporation, Tokyo (JP)

( * ) Notice: Subject to any disclaimer, the term of this patent is extended or adjusted under 35 U.S.C. 154(b) by 37 days.

This patent is subject to a terminal disclaimer.

(21) Appl. No.: 18/394,207

(22) Filed: Dec. 22, 2023

(65) Prior Publication Data

US 2024/0166949 A1 May 23, 2024

Related U.S. Application Data

(63) Continuation of application No. PCT/JP2022/024996, filed on Jun. 22, 2022.

(30) Foreign Application Priority Data

Jun. 23, 2021 (JP) ................................ 2021-104477

(51) Int. Cl.

| | |
|---|---|
| ***C09K 19/38*** | (2006.01) |
| ***C07C 69/76*** | (2006.01) |
| ***C07C 323/19*** | (2006.01) |
| ***C08F 222/26*** | (2006.01) |
| ***C09K 19/58*** | (2006.01) |
| ***G02B 5/30*** | (2006.01) |

(52) U.S. Cl.

CPC .......... *C09K 19/3852* (2013.01); *C07C 69/76* (2013.01); *C07C 323/19* (2013.01); *C08F 222/26* (2013.01); *C09K 19/588* (2013.01); *G02B 5/3016* (2013.01); *C08F 2800/20* (2013.01)

(58) Field of Classification Search

CPC ...................................................... C09K 19/58

See application file for complete search history.

(56) References Cited

U.S. PATENT DOCUMENTS

| | | | | |
|---|---|---|---|---|
| 4,730,032 | A | 3/1988 | Rossi et al. | |
| 12,054,660 | B2 * | 8/2024 | Fukushima | G02B 6/2726 |
| 2005/0012071 | A1 * | 1/2005 | Nishikawa | C09K 19/3444 252/299.61 |
| 2019/0177268 | A1 | 6/2019 | Fukushima et al. | |

(Continued)

FOREIGN PATENT DOCUMENTS

| | | |
|---|---|---|
| JP | 63-210110 A | 8/1988 |
| JP | 2005-35950 A | 2/2005 |

(Continued)

OTHER PUBLICATIONS

Jones et al. ("Rapid Solution and Solid Phase Syntheses of Oligo(1,4-phenylene ethynylene)s with Thioester Termini: Molecular Scale Wires with Alligator Clips, Derivation of Iterative Reaction Efficiencies on a Polymer Support" . Journal of Organic Chemistry (1997), vol. 62, No. 5, pp. 1388-1410). (Year: 1997).*

Sekiguchi et al. ("Preparation of a Cyclic Polyphenylene Array for a Chiral-Type Carbon Nanotube Segment" . BCSJ (2016), vol. 89, No. 10, pp. 1260-1275). (Year: 2016).*

Yan et al. ("Rigid, conjugated and shaped arylethynes as mediators for the assembly of gold nanoparticles". Journal of Material Chemistry. (2011), vol. 21, No. 6, pp. 1890-1901). (Year: 2011).*

Saito et al. ("Long-Range Anisotropic Structural Films and Fibers Formed from Lyotropic Liquid Crystal Gels Containing Hetero-Double Helices with C16 Terminal Groups". Langmuir, (2019), vol. 35 No. 14, pp. 2075-5080). (Year: 2019).*

Hahn et al., "A Practical and Efficient Synthesis of Uniform Conjugated Rod-Like Oligomers," Macromolecular Rapid Communications, vol. 42, 2021, 2000735, pp. 1-6.

(Continued)

*Primary Examiner* — Chanceity N Robinson

(74) *Attorney, Agent, or Firm* — Birch, Stewart, Kolasch & Birch, LLP

(57) ABSTRACT

A compound represented by General Formula (I), $A^1$ to $A^4$ each independently represent a non-aromatic ring group, an aromatic hydrocarbon ring group, or an aromatic heterocyclic group, which may have a substituent, Z represents —O—, —S—, —CHRCHR—, —OCHR—, —CHRO—, —CO—, —SO—, —$SO_2$—, —COO—, —OCO—, —CO—S—, —S—CO—, —O—CO—O—, —SCHR—, —CHRS—, —SO—CHR—, —CHR—SO—, —$SO_2$—CHR—, —CHR—$SO_2$—, —$CF_2O$—, —$OCF_2$—, —$CF_2S$—, —$SCF_2$—, —OCHRCHRO—, —SCHRCHRS—, —SO—CHRCHR—SO—, —$SO_2$—CHRCHR—$SO_2$—, —CH=CH—COO—, —CH=CH—OCO—, —COO—CH=CH—, —OCO—CH=CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR=CR—, —CR=N—, —N=CR—, —N=N—, —CR=N—N=CR—, —CF=CF—, —C≡C—, or a single bond, R represents a hydrogen atom or an alkyl group having 1 to 10 carbon atoms, and m1 represents an integer of 2 to 7.

(I)

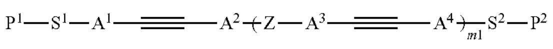

17 Claims, No Drawings

(56) References Cited

U.S. PATENT DOCUMENTS

| | | | | |
|---|---|---|---|---|
| 2021/0002556 | A1 | 1/2021 | Goto | |
| 2021/0149098 | A1 | 5/2021 | Sasata et al. | |
| 2021/0311352 | A1* | 10/2021 | Sasata | G02B 6/0023 |

FOREIGN PATENT DOCUMENTS

| | | | | | |
|---|---|---|---|---|---|
| WO | WO 2018/034216 | A1 | | 2/2018 | |
| WO | WO 2019/182129 | A1 | | 9/2019 | |
| WO | WO 2020/022496 | A1 | | 1/2020 | |
| WO | WO-2020122119 | A1 | * | 6/2020 | G02B 27/0081 |

OTHER PUBLICATIONS

International Preliminary Report on Patentability and English translation of the Written Opinion of the International Searching Authority (Forms PCT/IB/326, PCT/IB/373 and PCT/ISA/237) for International Application No. PCT/JP2022/024996, dated Jan. 4, 2024.

International Search Report (Form PCT/ISA/210) for International Application No. PCT/JP2022/024996, dated Sep. 6, 2022, with English translation.

Jones et al., "Rapid Solution and Solid Phase Syntheses of Oligo(1, 4-phenylene ethynylene)s with Thioester Termini: Molecular Scale Wires with Alligator Clips. Derivation of Iterative Reaction Efficiencies on a Polymer Support," J. Org. Chem., vol. 62, 1997, pp. 1388-1410.

Saito et al., "Long-Range Anisotropic Structural Films and Fibers Formed from Lyotropic Liquid Crystal Gels Containing Hetero-Double-Helices with C16 Terminal Groups," Langmuir, vol. 35, 2019, pp. 5075-5080.

Sekiguchi et al., "Preparation of a Cyclic Polyphenylene Array for a Chiral-Type Carbon Nanotube Segment," Bull. Chem. Soc. Jpn., vol. 89, 2016, pp. 1260-1275.

Yan et al., "Rigid, conjugated and shaped arylethynes as mediators for the assembly of gold nanoparticles," Journal of Materials Chemistry, vol. 21, 2011, pp. 1890-1901.

Hossain et al., "Dissipative Assembly of Macrocycles Comprising Multiple Transient Bonds," Angew. Chem. Int. Ed., vol. 59, 2020, pp. 13807-13813 (12 pages total).

Japanese Office Action for corresponding Japanese Application No. 2023-530109, dated Aug. 12, 2025, with English translation.

Jeong et al., "Regioselective Termination Reagents for Ring-Opening Alkyne Metathesis Polymerization," Journal of the American Chemical Society, vol. 139, 2017, pp. 15509-15514 (19 pages total).

Yu et al., "Reversible and Quantitative Denaturation of Amphiphilic Oligo(azobenzene) Foldamers," Angew. Chem. Int. Ed., vol. 50, 2011, pp. 1640-1643.

* cited by examiner

COMPOUND, COMPOSITION, CURED PRODUCT, OPTICALLY ANISOTROPIC BODY, OPTICAL ELEMENT, AND LIGHT GUIDE ELEMENT

CROSS REFERENCE TO RELATED APPLICATION

This is a continuation of International Application No. PCT/JP2022/024996 filed on Jun. 22, 2022, and claims priority from Japanese Patent Application No. 2021-104477 filed on Jun. 23, 2021, the entire disclosures of which are incorporated herein by reference.

BACKGROUND OF THE INVENTION

1. Field of the Invention

The present invention relates to a compound, a composition, a cured product, an optically anisotropic body, an optical element, and a light guide element.

2. Description of the Related Art

A compound having liquid crystallinity (hereinafter, also referred to as a "liquid crystal compound") and a composition having liquid crystallinity (hereinafter, also referred to as a "liquid crystal composition") can be applied to various use applications.

For example, WO2020/022496A describes that diffracted light with high diffraction efficiency can be obtained at a large diffraction angle by an optical element including an optically anisotropic layer consisting of a cured product of a composition containing a liquid crystal compound. WO2020/022496A describes that good diffraction efficiency can be obtained by using a liquid crystal compound having a high refractive index anisotropy Δn (hereinafter, also simply referred to as "Δn").

In addition, WO2018/034216A discloses a liquid crystal compound having a high Δn. Further, WO2018/034216A discloses a reflective film obtained by curing a composition containing a liquid crystal compound having a high Δn.

SUMMARY OF THE INVENTION

As described in WO2020/022496A and WO2018/034216A, a liquid crystal compound having a high Δn is useful for various use applications. In addition, for example, in a case of being mixed with another compound having liquid crystallinity, a compound having a high Δn can be used to form a liquid crystal composition having a high Δn even in a case where the compound itself does not have liquid crystallinity, which is useful in various use applications.

An object of the present invention is to provide a compound having a high refractive index anisotropy Δn and provide a composition, a cured product, an optically anisotropic body, an optical element, and a light guide element, each of which contains the compound.

As a result of intensive examination, the inventors of the present invention have found that the above object can be achieved by the following means.

<1>

A compound represented by General Formula (I).

(I)

$$P^1—S^1—A^1—\equiv—A^2\text{—}(Z—A^3—\equiv—A^4)_{m1}—S^2—P^2$$

In General Formula (I), $P^1$ and $P^2$ each independently represent a hydrogen atom or a substituent, $S^1$ and $S^2$ each independently represent a single bond or a divalent linking group, $A^1$ to $A^4$ each independently represent a non-aromatic ring group, an aromatic hydrocarbon ring group, or an aromatic heterocyclic group, which may have a substituent, a plurality of $A^3$'s and a plurality of $A^4$'s may be the same or different from each other, Z represents —O—, —S—, —CHRCHR—, —OCHR—, —CHRO—, —CO—, —SO—, $—SO_2—$, —COO—, —OCO—, —CO—S—, —S—CO—, —O—CO—O—, —SCHR—, —CHRS—, —SO—CHR—, —CHR—SO—, $—SO_2—CHR—$, $—CHR—SO_2—$, $—CF_2O—$, $—OCF_2—$, $—CF_2S—$, $—SCF_2—$, —OCHRCHRO—, —SCHRCHRS—, —SO—CHRCHR—SO—, $—SO_2—CHRCHR—SO_2—$, —CH═CH—COO—, —CH═CH—OCO—, —COO—CH═CH—, —OCO—CH═CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR═CR—, —CR═N—, —N═CR—, —N═N—, —CR═N—N═CR—, —CF═CF—, or a single bond, R represents a hydrogen atom or an alkyl group having 1 to 10 carbon atoms, a plurality of Z's may be the same or different from each other, in a case where a plurality of R's are present, the plurality of R's may be the same or different from each other, and m1 represents an integer of 2 to 7.

<2> The compound according to <1>, in which m1 in General Formula (I) represents 2.

<3> The compound according to <1> or <2>, in which at least any one of $P^1$ or $P^2$ in General Formula (I) represents any substituent selected from the group consisting of an alkyl group, an alkoxy group, an alkylcarbonyl group, an alkylcarbonyloxy group, and a polymerizable group.

<4> The compound according to any one of <1> to <3>, in which at least one of $P^1$ or $P^2$ in General Formula (I) represents a polymerizable group.

<5> The compound according to any one of <1> to <4>, in which at least one of $A^1$, . . . , or $A^4$ in General Formula (I) has at least one substituent selected from the group consisting of an alkyl group having 1 to 20 carbon atoms, an alkoxy group having 1 to 20 carbon atoms, an alkylamino group having 1 to 20 carbon atoms, an alkylthio group having 1 to 20 carbon atoms, an alkanoyl group having 1 to 20 carbon atoms, an alkanoyloxy group having 1 to 20 carbon atoms, an alkanoylamino group having 1 to 20 carbon atoms, an alkanoylthio group having 1 to 20 carbon atoms, an alkyloxycarbonyl group having 2 to 20 carbon atoms, an alkylaminocarbonyl group having 2 to 20 carbon atoms, an alkylthiocarbonyl group having 2 to 20 carbon atoms, a hydroxy group, an amino group, a mercapto group, a carboxy group, a sulfo group, an amide group, a cyano group, a nitro group, a halogen atom, and a polymerizable group, provided that in a case where the substituent has $—CH_2—$, at least one $—CH_2—$ contained in the substituent may be replaced with —O—, —CO—, —CH=CH—, or and in a case where the substituent has a hydrogen atom, at least one hydrogen atom contained in the substituent may be replaced with a fluorine atom.

<6> The compound according to any one of <1> to <5>, in which in General Formula (I), $S^1$ represents a group represented by General Formula (II), and $S^2$ represents a group represented by General Formula (III).

$$*—S—W^1—** \quad \text{(II)}$$

$$*—S—W^2—** \quad \text{(III)}$$

In General Formulae (II) and (III), $W^1$ and $W^2$ each independently represent an alkylene group having 1 to 15 carbon atoms, where one or more methylene groups contained in the alkylene group may be each independently replaced with —O—, —S—, or —CO—,

*'s each represent a bonding position to $A^1$ or $A^4$, which is directly linked to $S^1$ or $S^2$, and

**'s each represent a bonding position to $P^1$ or $P^2$.

<7> The compound according to any one of <1> to <6>, in which Z in General Formula (I) represents —CHRCHR—, —OCHR—, or —CHRO—, provided that R represents a hydrogen atom or an alkyl group having 1 to 10 carbon atoms, and in a case where a plurality of R's are present, the plurality of R's may be the same or different from each other.

<8> The compound according to any one of <1> to <7>, in which $P^1$ and $P^2$ in General Formula (I) each independently represent a group represented by any one of Formulae (P-1) to (P-19).

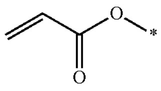
(P-1)

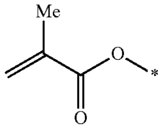
(P-2)

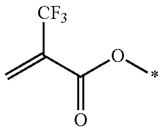
(P-3)

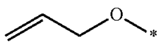
(P-4)

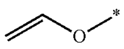
(P-5)

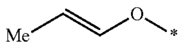
(P-6)

-continued

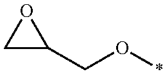
(P-7)

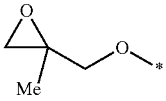
(P-8)

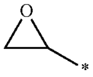
(P-9)

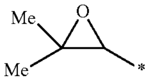
(P-10)

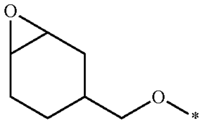
(P-11)

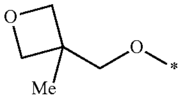
(P-12)

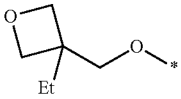
(P-13)

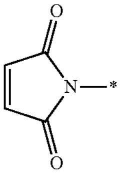
(P-14)

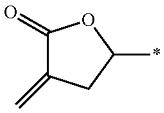
(P-15)

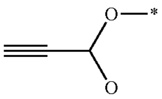
(P-16)

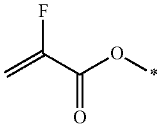
(P-17)

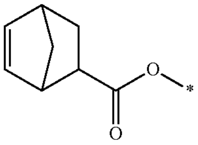
(P-18)

-continued (P-19)

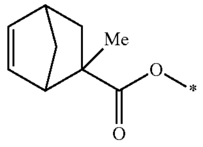

<9> The compound according to any one of <1> to <8>, in which the compound represented by General Formula (I) is a compound represented by General Formula (I-2).

anisotropic body, an optical element, and a light guide element, containing the compound, each of which contains the compound.

DESCRIPTION OF THE PREFERRED EMBODIMENTS

Hereinafter, embodiments of the present invention will be specifically described, but the present invention is not limited thereto. In the present specification, in a case where numerical values represent a value of physical properties, a value of characteristics, and the like, the description of (I-2)

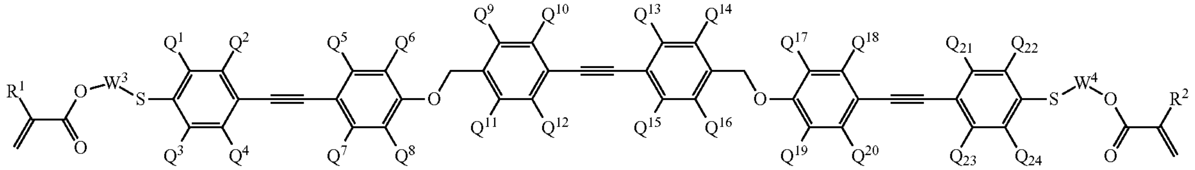

In General Formula (I-2), $R^1$ and $R^2$ each independently represent a hydrogen atom or a methyl group, $W^3$ and $W^4$ each independently represent an alkylene group having 1 to 6 carbon atoms, and $Q^1$ to $Q^{24}$ each independently represent a hydrogen atom, a fluorine atom, a chlorine atom, a nitro group, a cyano group, an alkyl group having 1 to 20 carbon atoms, an alkyloxycarbonyl group having 2 to 20 carbon atoms, or an alkylaminocarbonyl group having 2 to 20 carbon atoms.

<10> The compound according to any one of <1> to <9>, in which the compound has liquid crystallinity.

<11> A composition comprising the compound according to any one of <1> to <10>.

<12> The composition according to <11>, further comprising a polymerization initiator.

<13> The composition according to <11> or <12>, further comprising a chiral agent.

<14> The composition according to any one of <11> to <13>, in which the composition has liquid crystallinity.

<15> The composition according to any one of <11> to <14>, in which the composition is used for forming an optically anisotropic layer.

<16> A cured product that is obtained by curing the composition according to any one of <11> to <15>.

<17> An optically anisotropic body that is obtained by curing the composition according to any one of <11> to <15>.

<18> An optical element comprising:

an optically anisotropic layer formed from the composition according to any one of <11> to <15>, in which the optically anisotropic layer has an alignment pattern, and the alignment pattern is an alignment pattern in which an orientation of an optical axis, derived from a compound contained in the composition, continuously changes rotationally along at least one in-plane direction.

<19> A light guide element comprising the optical element according to <18> and a light guide plate.

According to the present invention, it is possible to provide a compound having a high refractive index anisotropy Δn, a composition, a cured product, an optically "(numerical value 1) to (numerical value 2)" means "(numerical value 1) or more and (numerical value 2) or less". In addition, in the present specification, the description of "(meth)acrylate" means "at least any one of acrylate or methacrylate". The same applies to "(meth)acrylic acid", "(meth)acryloyl", "(meth)acrylamide", "(meth)acryloyloxy".

[Compound Represented by General Formula (I)]

The compound represented by General Formula (I) will be described.

(I)

$$P^1—S^1—A^1—\equiv—A^2 \left( Z—A^3—\equiv—A^4 \right)_{m1} S^2—P^2$$

In General Formula (I), $P^1$ and $P^2$ each independently represent a hydrogen atom or a substituent, $S^1$ and $S^2$ each independently represent a single bond or a divalent linking group, $A^1$ to $A^4$ each independently represent a non-aromatic ring group, an aromatic hydrocarbon ring group, or an aromatic heterocyclic group, which may have a substituent, a plurality of $A^3$'s and a plurality of $A^4$'s may be the same or different from each other, Z represents —O—, —S—, —CHRCHR—, —OCHR—, —CHRO—, —CO—, —SO—, —$SO_2$—, —COO—, —OCO—, —CO—S—, —S—CO—, —O—CO—O—, —SCHR—, —CHRS—, —SO—CHR—, —CHR—SO—, —$SO_2$—CHR—, —CHR—$SO_2$—, —$CF_2$O—, —O$CF_2$—, —$CF_2$S—, —S$CF_2$—, —OCHRCHRO—, —SCHRCHRS—, —SO—CHRCHR—SO—, —$SO_2$—CHRCHR—$SO_2$—, —CH═CH—COO—, —CH═CH—OCO—, —COO—CH═CH—, —OCO—CH═CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR═CR—, —CR═N—, —N═CR—, —N═N—, —CR═N—N═CR—, —CF═CF—, or a single bond, R represents a hydrogen atom or an alkyl group having 1 to 10 carbon atoms, a plurality of Z's may be the same or different from each other, in a case where a plurality of R's are present, the plurality of R's may be the same or different from each other, and m1 represents an integer of 2 to 7.

In General Formula (I), m1 represents an integer of 2 to 7, preferably an integer of 2 to 5, more preferably 2 or 3, and still more preferably 2.

In General Formula (I), $P^1$ and $P^2$ each independently represent a hydrogen atom or a substituent.

In a case where $P^1$ and $P^2$ represent a substituent, the substituent is not particularly limited. Examples thereof include known substituents, examples of which include an alkyl group (preferably an alkyl group having 1 to 20 carbon atoms), an alkoxy group (preferably an alkoxy group having 1 to 20 carbon atoms), an alkylcarbonyl group (preferably an alkylcarbonyl group having 2 to 20 carbon atoms), an alkyloxycarbonyl group (preferably an alkyloxycarbonyl group having 2 to 20 carbon atoms), an alkylcarbonyloxy group (preferably an alkylcarbonyloxy group having 2 to 20 carbon atoms), an alkylamino group (preferably an alkylamino group having 1 to 20 carbon atoms), a dialkylamino group (preferably a dialkylamino group having 2 to 20 carbon atoms), an alkylamide group (preferably an alkylamide group having 2 to 20 carbon atoms), an alkenyl group (preferably an alkenyl group having 2 to 20 carbon atoms), an alkynyl group (preferably an alkynyl group having 2 to 20 carbon atoms), a halogen atom, a cyano group, a nitro group, an alkylthiol group, an N-alkylcarbamate group, and a polymerizable group. Each of the above-described groups may be further substituted with a substituent. For example, a hydrogen atom in the alkyl group may be substituted with a fluorine atom.

At least one of $P^1$ or $P^2$ preferably represents any substituent selected from the group consisting of an alkyl group, an alkoxy group, an alkylcarbonyl group, an alkylcarbonyloxy group, and a polymerizable group.

Due to the reason that in a case where an optically anisotropic layer is produced from a composition containing a compound represented by General Formula (I), the alignment state of the compound represented by General Formula (I) can be fixed, or the durability of the optically anisotropic layer can be improved, it is preferable that at least any one of $P^1$ or $P^2$ represents a polymerizable group. Due to the reason that the reactivity is more excellent, it is more preferable that both $P^1$ and $P^2$ represent a polymerizable group.

The polymerizable group is not particularly limited, and examples thereof include a known polymerizable group. From the viewpoint of reactivity, a functional group that can be subjected to an addition polymerization reaction is preferable, and a polymerizable ethylenically unsaturated group or a cyclic polymerizable group is more preferable. Examples of the polymerizable group include a (meth)acryloyloxy group, a vinyl group, a maleimide group, a styryl group, an allyl group, an epoxy group, an oxetane group, and a group containing this group. A hydrogen atom in each of the above groups may be substituted with another substituent such as a halogen atom.

Suitable specific examples of the polymerizable group include a group represented by any one of Formulae (P-1) to (P-19) below. In the following formulae, * represents a bonding position, Me represents a methyl group, and Et represents an ethyl group.

The polymerizable group is preferably a (meth)acryloyloxy group.

$P^1$ and $P^2$ in General Formula (I) each independently preferably represent a group represented by any one of Formulae (P-1) to (P-19) and more preferably represent a (meth)acryloyloxy group.

(P-1)

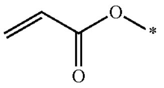

(P-2)

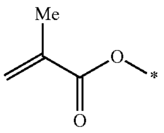

(P-3)

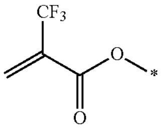

(P-4)

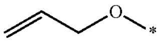

(P-5)

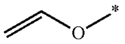

(P-6)

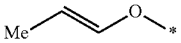

(P-7)

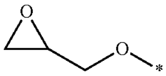

(P-8)

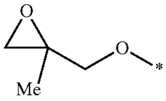

(P-9)

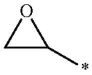

(P-10)

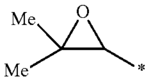

(P-11)

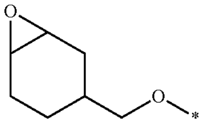

(P-12)

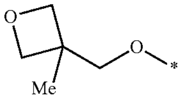

(P-13)

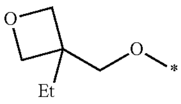

-continued (P-14)

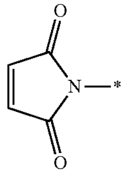

(P-15)

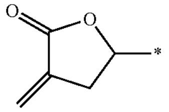

(P-16)

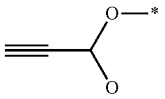

(P-17)

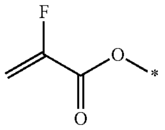

(P-18)

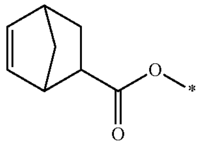

(P-19)

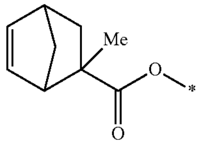

In General Formula (I), $A^1$ to $A^4$ each independently represent a non-aromatic ring group, an aromatic hydrocarbon ring group, or an aromatic heterocyclic group which may have a substituent.

A plurality of $A^3$'s and a plurality of $A^4$'s may be the same or different from each other.

$A^1$ to $A^4$ are a divalent group.

In a case where $A^1$ to $A^4$ represent a non-aromatic ring group, the non-aromatic ring group is not particularly limited. However, it is preferably a cycloalkylene group and more preferably a cycloalkylene group having 3 to 20 carbon atoms.

In a case where $A^1$ to $A^4$ represent an aromatic hydrocarbon ring group, the aromatic hydrocarbon ring group is not particularly limited. However, it is preferably an arylene group, more preferably an arylene group having 6 to 20 carbon atoms, still more preferably an arylene group having 6 to 10 carbon atoms, and particularly preferably a phenylene group.

In a case where $A^1$ to $A^4$ represent an aromatic heterocyclic group, the aromatic heterocyclic group is not particularly limited. However, it is preferably a heteroarylene group, more preferably a heteroarylene group having 3 to 20 carbon atoms, and still more preferably a heteroarylene group having 3 to 10 carbon atoms. The heteroatom contained in the heteroarylene group is preferably at least one selected from the group consisting of a nitrogen atom, an oxygen atom, and a sulfur atom.

It is preferable that $A^1$ to $A^4$ each independently represent an aromatic hydrocarbon ring group which may have a substituent.

The substituent which may be contained in $A^1$ to $A^4$ is not particularly limited. However, examples thereof include a halogen atom (preferably a fluorine atom or a chlorine atom), an alkyl group (preferably an alkyl group having 1 to 20 carbon atoms), an alkoxy group (preferably an alkoxy group having 1 to 20 carbon atoms), an aryl group (preferably an aryl group having 6 to 20 carbon atoms), a nitro group, a cyano group, an isothiocyanate group, a hydroxy group, an amino group, a carboxy group, a sulfonamide group, an N-sulfonylamide group, an acyl group (preferably an acyl group having 2 to 20 carbon atoms), an acyloxy group (preferably an acyloxy group having 2 to 20 carbon atoms), an alkyloxycarbonyl group (preferably an alkyloxycarbonyl group having 2 to 20 carbon atoms), and an alkylaminocarbonyl group (preferably, an alkylaminocarbonyl group having 2 to 20 carbon atoms). Each of the above-described groups may be further substituted with a substituent. For example, a hydrogen atom in the alkyl group may be substituted with a fluorine atom.

It is preferable that at least one of $A^1$, . . . , or $A^4$ in General Formula (I) has a substituent.

In a case where at least one of $A^1$, . . . , or $A^4$ in General Formula (I) has a substituent, the substituent is also referred to as a substituent L.

It is more preferable that at least one of $A^1$, . . . , $A^4$ in General Formula (I) has at least one substituent selected from the group consisting of an alkyl group having 1 to 20 carbon atoms, an alkoxy group having 1 to 20 carbon atoms, an alkylamino group having 1 to 20 carbon atoms, an alkylthio group having 1 to 20 carbon atoms, an alkanoyl group having 1 to 20 carbon atoms, an alkanoyloxy group having 1 to 20 carbon atoms, an alkanoylamino group having 1 to 20 carbon atoms, an alkanoylthio group having 1 to 20 carbon atoms, an alkyloxycarbonyl group having 2 to 20 carbon atoms, an alkylaminocarbonyl group having 2 to 20 carbon atoms, an alkylthiocarbonyl group having 2 to 20 carbon atoms, a hydroxy group, an amino group, a mercapto group, a carboxy group, a sulfo group, an amide group, a cyano group, a nitro group, a halogen atom, and a polymerizable group. However, in a case where the substituent has $—CH_2—$, at least one $—CH_2—$ contained in the substituent may be replaced with —O—, —CO—, —CH═CH—, or —C≡C—. In addition, in a case where the substituent has a hydrogen atom, at least one hydrogen atom contained in the substituent may be replaced with a fluorine atom.

The substituent L is more preferably at least one substituent selected from the group consisting of an alkyl group having 1 to 10 carbon atoms, an alkoxy group having 1 to 10 carbon atoms, an alkylamino group having 1 to 10 carbon atoms, an alkylthio group having 1 to 10 carbon atoms, an alkanoyl group having to 10 carbon atoms, an alkanoyloxy group having 1 to 10 carbon atoms, an alkanoylamino group having 1 to 10 carbon atoms, an alkanoylthio group having 1 to 10 carbon atoms, an alkyloxycarbonyl group having 2 to 10 carbon atoms, an alkylaminocarbonyl group having 2 to 10 carbon atoms, an alkylthiocarbonyl group having 2 to 10 carbon atoms, a hydroxy group, an amino group, a mercapto group, a carboxy group, a sulfo group, an amide group, a cyano group, a nitro group, and a halogen atom, still more preferably at least one substituent selected from the group consisting of a fluorine atom, an alkyl group having 1 to 10 carbon atoms, an alkyloxycarbonyl group having 2 to 10 carbon atoms, and an alkylaminocarbonyl group having 2 to 10 carbon atoms, and particularly preferably at least one substituent selected from the group consisting of an alkyl group having 1 to 10 carbon atoms and an alkyloxycarbonyl group having 2 to 10 carbon atoms.

The number of carbon atoms of the alkyl group is more preferably 1 to 5 and still more preferably 1 to 3. The number of carbon atoms of the alkyloxycarbonyl group is more preferably 2 to 5 and still more preferably 2 or 3. The number of carbon atoms of the alkylaminocarbonyl group is more preferably 2 to 5 and still more preferably 2 or 3.

In General Formula (I), $S^1$ and $S^2$ each independently represent a single bond or a divalent linking group.

In a case where $S^1$ and $S^2$ represent a divalent linking group, the divalent linking group is preferably an alkylene group (preferably an alkylene group having 1 to 20 carbon atoms), an alkenylene group (preferably an alkenylene group having 2 to 20 carbon atoms), —O—, —S—, —CO—, —SO—, —$SO_2$—, —COO—, —OCO—, —CO—S—, —S—CO—, —O—CO—O—, or a divalent linking group obtained by combining a plurality of these.

It is preferable that $S^1$ represents a group represented by General Formula (II), and $S^2$ represents a group represented by General Formula (III).

Since the group represented by General Formula (II) and the group represented by General Formula (III) contain a sulfur atom, it is possible to further increase Δn of the compound represented by General Formula (I) in a case where $S^1$ and $S^2$ are these groups.

$$*\text{—S—}W^1\text{—}** \qquad \text{(II)}$$

$$*\text{—S—}W^2\text{—}** \qquad \text{(III)}$$

In General Formulae (II) and (III), $W^1$ and $W^2$ each independently represent an alkylene group having 1 to 15 carbon atoms, where one or more methylene groups contained in the alkylene group may be each independently replaced with —O—, —S—, or —CO—,

*'s each represent a bonding position to $A^1$ or $A^4$, which is directly linked to $S^1$ or $S^2$, and

**'s each represent a bonding position to $P^1$ or $P^2$.

$W^1$ and $W^2$ each independently represent an alkylene group having 1 to 15 carbon atoms, and $W^1$ and $W^2$ preferably represent an alkylene group having 1 to 10 carbon atoms and more preferably represent an alkylene group having 1 to 5 carbon atoms.

Z in General Formula (I) represents —O—, —S—, —CHRCHR—, —OCHR—, —CHRO—, —CO—, —SO—, —$SO_2$—, —COO—, —OCO—, —CO—S—, —S—CO—, —O—CO—O—, —SCHR—, —CHRS—, —SO—CHR—, —CHR—SO—, —$SO_2$—CHR—, —CHR—$SO_2$—, —$CF_2$O—, —O$CF_2$—, —$CF_2$S—, —S$CF_2$—, —OCHRCHRO—, —SCHRCHRS—, —SO—CHRCHR—SO—, —$SO_2$—CHRCHR—$SO_2$—, —CH=CH—COO—, —CH=CH—OCO—, —COO—CH=CH—, —OCO—CH=CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR=CR—, —CR=N—, —N=CR—, —N=N—, —CR=N—N=CR—, —CF=CF—, or a single bond.

R represents a hydrogen atom or an alkyl group having 1 to 10 carbon atoms.

A plurality of Z's may be the same or different from each other.

In a case where a plurality of R's are present, the plurality of R's may be the same or different from each other.

Z preferably represents —CHRCHR—, —OCHR—, or —CHRO—, and more preferably represents —OCHR— or —CHRO—. R is as described above.

R represents a hydrogen atom or an alkyl group having 1 to 10 carbon atoms, and it preferably represents a hydrogen atom or an alkyl group having 1 to 6 carbon atoms and more preferably represents a hydrogen atom.

The compound represented by General Formula (I) is preferably a compound represented by General Formula (I-2).

(I-2)

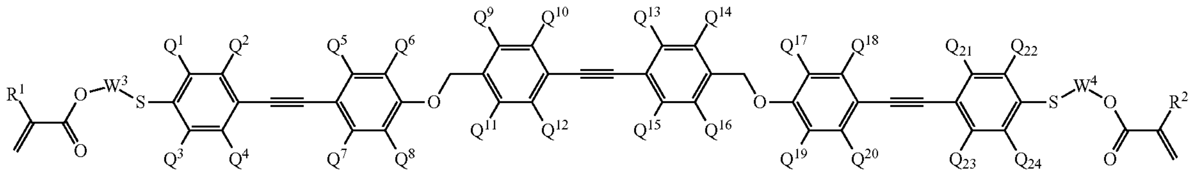

In General Formula (I-2), $R^1$ and $R^2$ each independently represent a hydrogen atom or a methyl group, $W^3$ and $W^4$ each independently represent an alkylene group having 1 to 6 carbon atoms, and $Q^1$ to $Q^{24}$ each independently represent a hydrogen atom or a substituent.

$R^1$ and $R^2$ preferably represent a hydrogen atom.

$W^3$ and $W^4$ each independently preferably represent an alkylene group having 2 to 4 carbon atoms.

$Q^1$ to $Q^{24}$ each independently represent a hydrogen atom or a substituent, and the specific example of the substituent is the same as the substituent (substituent L) in a case where at least one of $A^1$, . . . , or $A^4$ in General Formula (I) has a substituent.

It is preferable that $Q^1$ to $Q^{24}$ each independently represent a hydrogen atom, a fluorine atom, a chlorine atom, a nitro group, a cyano group, an alkyl group having 1 to 20 carbon atoms, an alkyloxycarbonyl group having 2 to 20 carbon atoms, or an alkylaminocarbonyl group having 2 to 20 carbon atoms.

$Q^1$ to $Q^{24}$ each independently preferably represent a hydrogen atom, a fluorine atom, a chlorine atom, a nitro group, a cyano group, an alkyl group having 1 to 10 carbon atoms, an alkyloxycarbonyl group having 2 to 10 carbon atoms, or an alkylaminocarbonyl group having 2 to 10 carbon atoms, still more preferably a hydrogen atom, a fluorine atom, an alkyl group having 1 to 10 carbon atoms, an alkyloxycarbonyl group having 2 to 10 carbon atoms, or an alkylaminocarbonyl group having 2 to 10 carbon atoms, and particularly preferably a hydrogen atom, an alkyl group having 1 to 10 carbon atoms, or an alkyloxycarbonyl group having 2 to 10 carbon atoms.

The number of carbon atoms of the alkyl group is more preferably 1 to 5 and still more preferably 1 to 3. The number of carbon atoms of the alkyloxycarbonyl group is more preferably 2 to 5 and still more preferably 2 or 3. The number of carbon atoms of the alkylaminocarbonyl group is more preferably 2 to 5 and still more preferably 2 or 3.

It is preferable that at least one of $Q^1$, . . . , or $Q^8$ represents a substituent. It is preferable that at least one of $Q^9$, . . . , or $Q^{16}$ represents a substituent. It is preferable that at least one of $Q^{17}$, . . . , or $Q^{24}$ represents a substituent. It is particularly preferable that $Q^8$ and $Q^{19}$ represent a substituent.

Specific examples of the compound represented by General Formula (I) are shown below, which are not limited thereto. In the structural formulae, Me represents a methyl group.

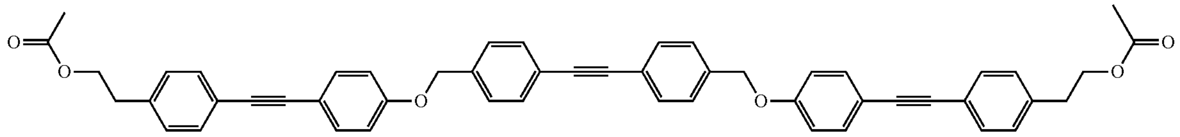

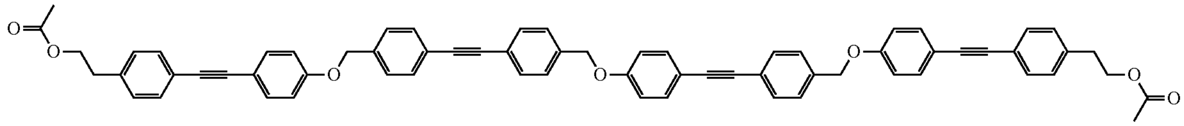

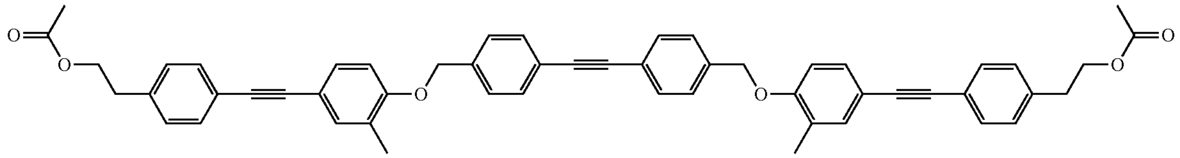

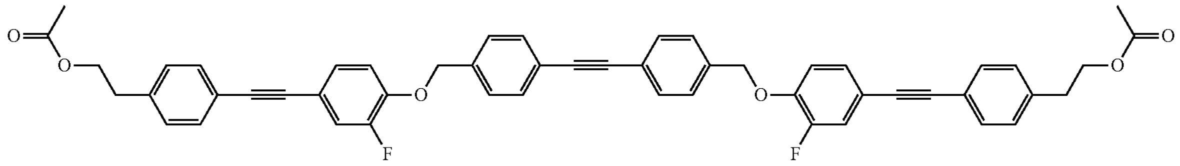

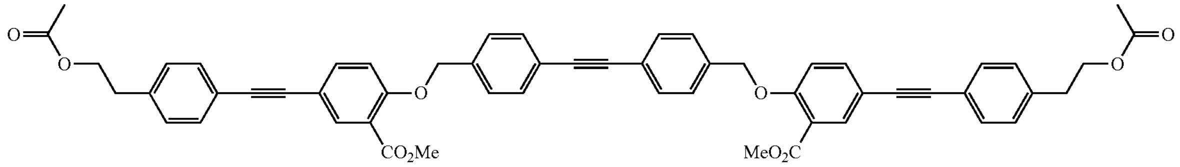

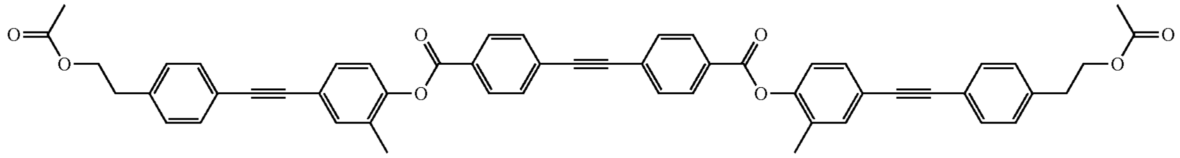

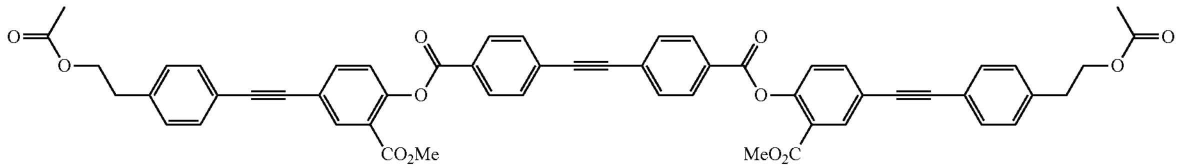

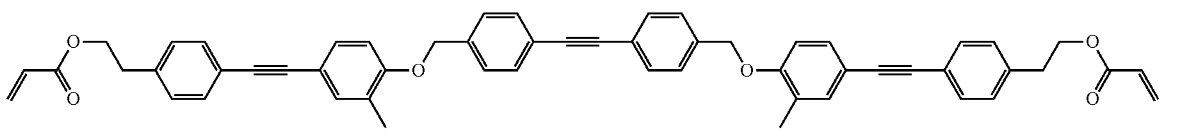

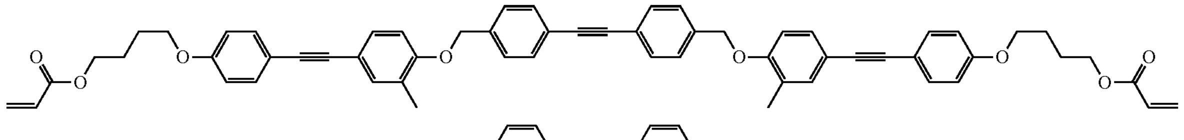

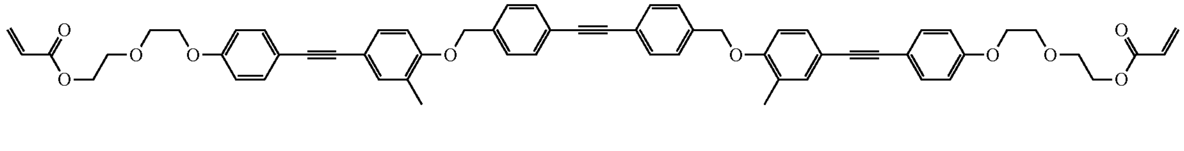

-continued

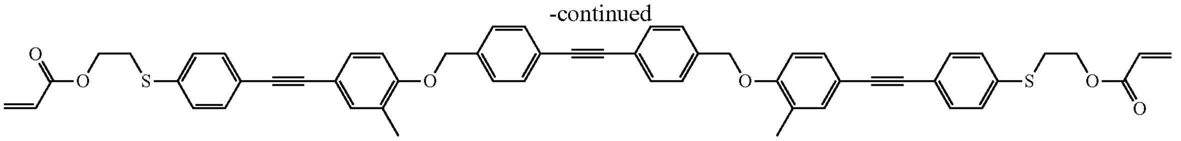

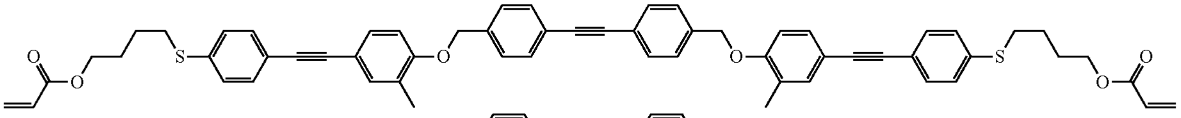

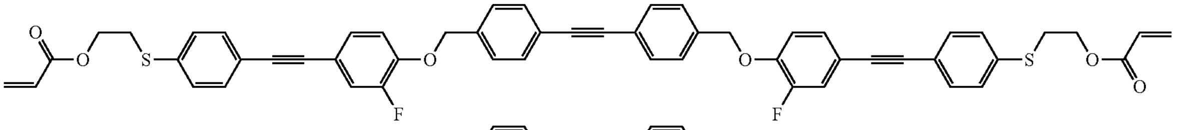

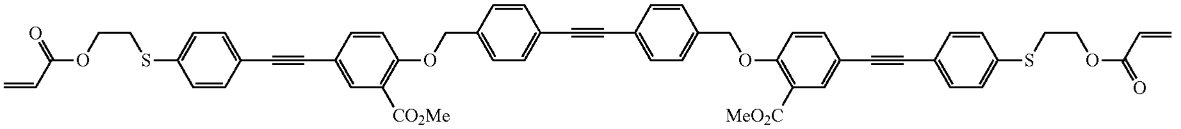

The compound represented by General Formula (I) can be synthesized by referring to or combining known methods. Specific synthesis examples of the compound represented by General Formula (I) will be described in Examples described later.

The compound represented by General Formula (I) may have or may not have liquid crystallinity; however, it preferably has liquid crystallinity.

In a case where the compound represented by General Formula (I) has liquid crystallinity, it is easy to align the compound represented by General Formula (I) and it is possible to easily produce a desired alignment pattern, which is preferable, in a case where an optically anisotropic layer is produced from a composition containing the compound represented by General Formula (I).

However, for example, in a case of being mixed with another compound having liquid crystallinity, the compound represented by General Formula (I) can be used to form a liquid crystal composition even in a case where the compound itself does not have liquid crystallinity, whereby a desired alignment pattern can be produced.

That the compound has liquid crystallinity means that the compound has properties of exhibiting a mesophase between a crystal phase (a low temperature side) and an isotropic phase (a high temperature side) in a case where the temperature is changed. As a specific observation method, optical anisotropy and fluidity derived from the liquid crystal phase can be checked by carrying out an observation under a polarization microscope while heating or lowering the temperature of the compound with a hot stage or the like.

[Composition Containing Compound Represented by General Formula (I)]

A composition containing the compound represented by General Formula (I) (hereinafter, also referred to as a "composition according to the embodiment of the present invention") will be described.

The content of the compound represented by General Formula (I) in the composition according to the embodiment of the present invention is not particularly limited; however, it is preferably 5% to 100% by mass, more preferably 20% to 90% by mass, and still more preferably 40% to 80% by mass, with respect to the total mass of the solid contents in the composition.

The solid contents mean components (non-volatile contents) other than the solvent in the composition. In a case of components other than the solvent, the components are regarded as the solid contents even in a case where they are components having properties of a liquid.

In the composition according to the embodiment of the present invention, one kind of the compound represented by General Formula (I) may be used alone, or two or more kinds thereof may be used. In a case where two or more kinds are used, the total content thereof is preferably within the above-described range.

The composition according to the embodiment of the present invention may have or may not have liquid crystallinity; however, it preferably has liquid crystallinity.

In a case where the composition according to the embodiment of the present invention has liquid crystallinity, it is easy to align the compound in the composition, and it is possible to easily produce a desired alignment pattern, which is preferable, in a case where an optically anisotropic layer is produced from the composition.

That the composition has liquid crystallinity means that the composition has properties of exhibiting a mesophase between a crystal phase (a low temperature side) and an isotropic phase (a high temperature side) in a case where the temperature is changed. As a specific observation method, optical anisotropy and fluidity derived from the liquid crystal phase can be checked by carrying out an observation under a polarization microscope while heating or lowering the temperature of the composition with a hot stage or the like.

The composition according to the embodiment of the present invention is preferably a composition for forming an optically anisotropic layer.

The composition according to the embodiment of the present invention may contain other components in addition to the compound represented by General Formula (I).

Hereinafter, the other components will be described.

<Another Liquid Crystal Compound>

The composition according to the embodiment of the present invention may contain a liquid crystal compound (also referred to as "another liquid crystal compound") that is not a compound represented by General Formula (I).

The other liquid crystal compound may be a rod-like liquid crystal compound or a disk-like liquid crystal compound; however, it is preferably a rod-like liquid crystal compound. In addition, the other liquid crystal compound is preferably a liquid crystal compound having a polymerizable group (other polymerizable liquid crystal compound).

Examples of the rod-like liquid crystal compound as the other liquid crystal compound include a rod-like nematic liquid crystal compound. The rod-like nematic liquid crystal compounds are preferably azomethines, azoxys, cyanobiphenyls, cyanophenyl esters, benzoic acid esters, cyclohexanecarboxylic acid phenyl esters, cyanophenylcyclohexanes, cyano-substituted phenylpyrimidines, alkoxy-substituted phenylpyrimidines, phenyl dioxanes, tolans, or alkenylcyclohexylbenzonitriles. As the other liquid crystal compound, not only a liquid crystal compound having a low molecular weight but also a polymer liquid crystal compound can be used.

The liquid crystal compound having a polymerizable group can be obtained by introducing the polymerizable group into the liquid crystal compound. Examples of the polymerizable group include the polymerizable group exemplified as $P^1$ and $P^2$ of General Formula (I).

The liquid crystal compound having polymerizable groups preferably has 1 to 6 polymerizable groups and more preferably 1 to 3 polymerizable groups.

It is preferable that the other liquid crystal compound has a high refractive index anisotropy Δn, and specifically, the refractive index anisotropy Δn is preferably 0.15 or more, more preferably 0.18 or more, and still more preferably 0.22 or more. The upper limit thereof is not particularly limited; however, it is 0.60 or less in many cases.

In addition, by mixing the compound represented by General Formula (I) with the other liquid crystal compound and using the resultant mixture, the crystallization temperature as a whole can be significantly lowered.

Examples of other liquid crystal compounds include compounds disclosed in Makromol. Chem., Vol. 190, page 2255 (1989), Advanced Materials, Vol. 5, page 107 (1993), U.S. Pat. Nos. 4,683,327A, 4,983,479A, 5,622,648A, 5,770,107A, WO95/22586A, WO95/24455A, WO97/00600A, WO98/23580A, WO98/52905A, JP1989-272551A (JP-H1-272551A), JP1994-16616A (JP-H6-16616A), JP1995-110469A (JP-H7-110469A), JP1999-80081A (JP-H11-80081A), JP2001-328973A.

In a case where the composition according to the embodiment of the present invention contains another liquid crystal compound, the content of the other liquid crystal compound in the composition is not particularly limited; however, it is preferably 95% by mass or less, more preferably 10% to 80% by mass, still more preferably 20% to 70% by mass, and particularly preferably 30% to 60% by mass, with respect to the total mass of the solid contents in the composition.

In the composition according to the embodiment of the present invention, one kind of another liquid crystal compound may be used alone, or two or more kinds thereof may be used. In a case where two or more kinds are used, the total content thereof is preferably within the above-described range.

<Polymerization Initiator>

The composition according to the embodiment of the present invention may contain a polymerization initiator.

The polymerization initiator is preferably a photopolymerization initiator which is capable of initiating a polymerization reaction by ultraviolet irradiation. Examples of the photopolymerization initiator include an α-carbonyl compound, an acyloin ether, an α-hydrocarbon-substituted aromatic acyloin compound, a polynuclear quinone compound, a phenazine compound, and an oxadiazole compound. In addition, a compound having an oxime ester structure is also preferable.

In a case where the composition according to the embodiment of the present invention contains a polymerization initiator, the content of the polymerization initiator in the composition is not particularly limited; however, it is preferably 0.1% to 20% by mass, and it is more preferably 1% to 8% by mass, with respect to the total mass of the compound represented by General Formula (I) (with respect to the total mass of the compound represented by General Formula (I) and another liquid crystal compound in a case where the composition contains the other liquid crystal compound).

In the composition according to the embodiment of the present invention, one kind of polymerization initiator may be used alone, or two or more kinds thereof may be used. In a case where two or more kinds are used, the total content thereof is preferably within the above-described range.

<Surfactant>

The composition according to the embodiment of the present invention may contain a surfactant that contributes to the formation of a stable or rapid liquid crystal phase (for example, a nematic phase, a cholesteric phase).

Examples of the surfactant include a fluorine-containing (meth)acrylate-based polymer, compounds represented by General Formulae (X1) to (X3) disclosed in WO2011/162291A, compounds represented by General Formula (I) disclosed in paragraphs 0082 to 0090 of JP2014-119605A, and compounds disclosed in paragraphs 0020 to 0031 of JP2013-47204A.

Examples of the fluorine-containing (meth)acrylate-based polymer that can be used as a surfactant also include polymers disclosed in paragraphs 0018 to 0043 of JP2007-272185A.

In a case where the composition according to the embodiment of the present invention contains a surfactant, the content of the surfactant is not particularly limited; however, it is preferably 0.001% to 10% by mass and more preferably 0.05% to 3% by mass with respect to the total mass of the compound represented by General Formula (I) (with respect to the total mass of the compound represented by General Formula (I) and another liquid crystal compound in a case where the composition contains the other liquid crystal compound).

In the composition according to the embodiment of the present invention, one kind of surfactant may be used alone, or two or more kinds thereof may be used. In a case where two or more kinds are used, the total content thereof is preferably within the above-described range.

<Chiral Agent>

The composition according to the embodiment of the present invention may contain a chiral agent. In a case where the composition according to the embodiment of the present invention contains a chiral agent, a cholesteric phase can be formed.

The kind of the chiral agent is not particularly limited. The chiral agent may be liquid crystalline or non-liquid crystalline. The chiral agent generally contains a chiral carbon atom. However, an axially chiral compound or a planar chiral compound, which does not contain any asymmetric carbon atom, can also be used as the chiral agent. Examples of the axially chiral compound or the planar chiral compound include binaphthyl, helicene, paracyclophane, and a derivative thereof. The chiral agent may have a polymerizable group.

In a case where the composition according to the embodiment of the present invention contains a chiral agent, the content of the chiral agent in the composition is not particularly limited; however, it is preferably 0.1% to 15% by mass and more preferably 1.0% to 10% by mass with respect to the total mass of the compound represented by General Formula (I) (with respect to the total mass of the compound represented by General Formula (I) and another liquid crystal compound in a case where the composition contains the other liquid crystal compound).

In the composition according to the embodiment of the present invention, one kind of chiral agent may be used alone, or two or more kinds thereof may be used. In a case where two or more kinds are used, the total content thereof is preferably within the above-described range.

<Solvent>

The composition of the embodiment of the present invention may contain a solvent. The solvent is preferably a solvent capable of dissolving each component of the composition according to the embodiment of the present invention, and examples thereof include chloroform and methyl ethyl ketone. In a case where the composition according to the embodiment of the present invention contains the solvent, the content of the solvent in the composition is such an amount that the concentration of solid contents of the composition is preferably 0.5% to 20% by mass and more preferably 1% to 10% by mass.

In the composition according to the embodiment of the present invention, one kind of solvent may be used alone, or two or more kinds thereof may be used. In a case where two or more kinds are used, the total content thereof is preferably within the above-described range.

In addition to the above, the composition according to the embodiment of the present invention may also contain other components such as an antioxidant, an ultraviolet absorber, a sensitizer, a stabilizer, a plasticizer, a chain transfer agent, a polymerization inhibitor, an anti-foaming agent, a leveling agent, a thickener, a flame retardant, a surfactant, a dispersing agent, and a coloring material such as a dye or a pigment.

In addition, it is also preferable that the optically anisotropic layer is made to be responsive to substantially a wide range of wavelengths of incident light by imparting a twisting component to the composition according to the embodiment of the present invention or by laminating different retardation layers. For example, JP2014-089476A or the like discloses a method of realizing a λ/2 plate having a wide-range pattern by laminating two liquid crystal layers having different twisted directions in an optically anisotropic layer, which can be preferably used in the optical element according to the embodiment of the present disclosure.

An optical element according to the embodiment of the present invention, which will be described later, is preferably produced by dissolving a composition containing the compound represented by General Formula (I) in a solvent and applying the dissolved composition.

In the resin composition according to the embodiment of the present invention, due to the reason that the composition according to the embodiment of the present invention has a high Δn and the diffraction efficiency of the optical element to be produced is further improved, the precipitation concentration of the composition in a cyclopentanone solution at 25° C. (the concentration at which the precipitation of the compound occurs) is preferably more than 5% by mass and more preferably 6% by mass or more.

[Cured Product and Optically Anisotropic Body]

A cured product that is obtained by curing the composition according to the embodiment of the present invention, and an optically anisotropic body will be described.

A method of curing (polymerizing and curing) the composition according to the embodiment of the present invention is not particularly limited, and a known method can be adopted. Examples thereof include an aspect having a step X of bringing a predetermined substrate into contact with a composition to form a composition layer on the substrate and a step Y of subjecting the composition layer to a heat treatment so that the compound represented by General Formula (I) is aligned and then carrying out a curing treatment. According to the present aspect, the compound represented by General Formula (I) can be immobilized in an aligned state, whereby an optically anisotropic body (for example, an optically anisotropic layer) can be formed.

Hereinafter, procedures for the step X and the step Y will be described in detail.

The step X is a step of bringing a predetermined substrate into contact with a composition to form a composition layer on the substrate. The kind of the substrate to be used is not particularly limited, and examples thereof include known substrates (for example, a resin substrate, a glass substrate, a ceramic substrate, a semiconductor substrate, and a metal substrate).

The method of bringing a substrate into contact with a composition is not particularly limited, and examples thereof include a method of applying a composition onto a substrate and a method of immersing a substrate in a composition.

It is noted that after bringing a substrate into contact with a composition, as necessary, a drying treatment may be carried out in order to remove a solvent from the composition layer on the substrate.

The step Y is a step of subjecting the composition layer to a heat treatment so that the compound represented by General Formula (I) invention is aligned, and then carrying out a curing treatment.

In a case where the composition layer is subjected to a heat treatment, the compound represented by General Formula (I) is aligned and a liquid crystal phase is formed. For example, in a case where the composition layer contains a chiral agent, a cholesteric liquid crystalline phase is formed.

The conditions for the heat treatment are not particularly limited, and optimal conditions are selected depending on the kind of the compound represented by General Formula (I).

The method for the curing treatment is not particularly limited, and examples thereof include a photo-curing treatment and a thermal-curing treatment. Among these, a light irradiation treatment is preferable, and an ultraviolet irradiation treatment is more preferable.

For ultraviolet irradiation, a light source such as an ultraviolet lamp is used.

The cured product that is obtained by the above treatment corresponds to a layer that is obtained by immobilizing a liquid crystal phase. In particular, in a case where the composition contains a chiral agent, a layer is formed in which a cholesteric liquid crystalline phase is immobilized.

It is noted that these layers do not need to exhibit liquid crystallinity anymore. More specifically, for example, as a state in which the cholesteric liquid crystalline phase is "immobilized", the most typical and preferred aspect is a state in which the alignment of the compound represented by General Formula (I) which is in the cholesteric liquid crystalline phase is retained. More specifically, it is preferably a state in which within a temperature range of usually 0° C. to 50° C., or −30° C. to 70° C. under the more severe conditions, no fluidity is exhibited in the layer, no changes in alignment form occur due to an external field or an external force, and a fixed alignment form can be kept stably and continuously.

[Optical Element]

The optical element according to the embodiment of the present invention is an optical element that has an optically anisotropic layer formed from the above-described composition according to the embodiment of the present invention, where the optically anisotropic layer has an alignment pattern, and the alignment pattern is an alignment pattern in which an orientation of an optical axis, derived from a compound contained in the composition, continuously changes rotationally along at least one in-plane direction.

It is preferable that the alignment pattern is an alignment pattern in which the orientation of the optical axis, derived from the compound represented by General Formula (I), continuously changes rotationally along at least one in-plane direction, or an alignment pattern in which the orientation of the optical axis, derived from the compound represented by General Formula (I) and the other liquid crystal compound, continuously changes rotationally along at least one in-plane direction.

The optical element according to the embodiment of the present invention has an alignment pattern in which the orientation of the optical axis continuously changes rotationally along at least one in-plane direction, and thus it can diffract the light incident on the optical element. Since the compound represented by General Formula (I) is a compound having a high refractive index anisotropy $\Delta n$, the diffraction efficiency can be increased.

For the optical element, the description of paragraphs to of WO2020/022496A can be referred to.

The optical element according to the embodiment of the present invention can be applied as an optical member such as an augmented reality (AR) image projection device.

[Light Guide Element]

A light guide element according to the embodiment of the present invention includes the above-described optical element and a light guide plate.

EXAMPLES

Hereinafter, the present invention will be described more specifically with reference to Examples and Comparative Examples. In Examples below, the material, the using amount, the proportion, the details of treatment, the treatment procedure, and the like can be suitably modified without departing from the scope of the present invention. Accordingly, the scope of the present invention should not be interpreted restrictively by the following specific examples.

<Synthesis of Compound A-1>

A compound A-1 was synthesized according to Synthesis Example 6 of WO2019/182129A. The compound A-1 is a polymerizable liquid crystal compound.

A-1

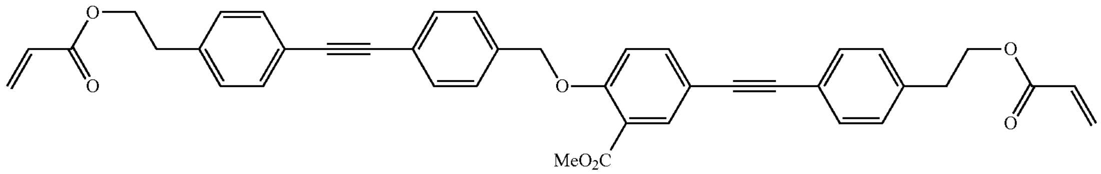

Synthesis Example 1: Synthesis of Compound B-1

The compound B-1 was synthesized according to the following scheme. It is noted that a compound 1 and a compound 5 was synthesized according to WO2019/182129A.

Ms represents a methanesulfonyl group ($-SO_2CH_3$) and TMS represents a trimethylsilyl group ($-Si(CH_3)_3$).

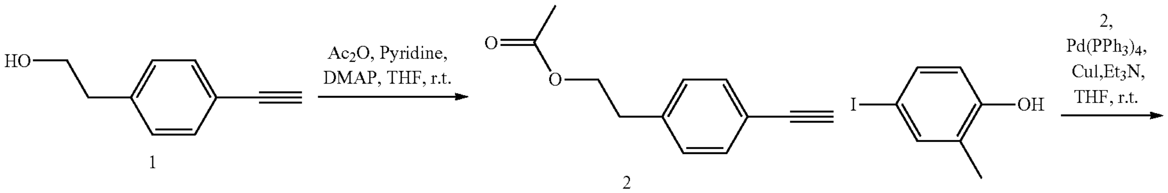

1

2

3

-continued

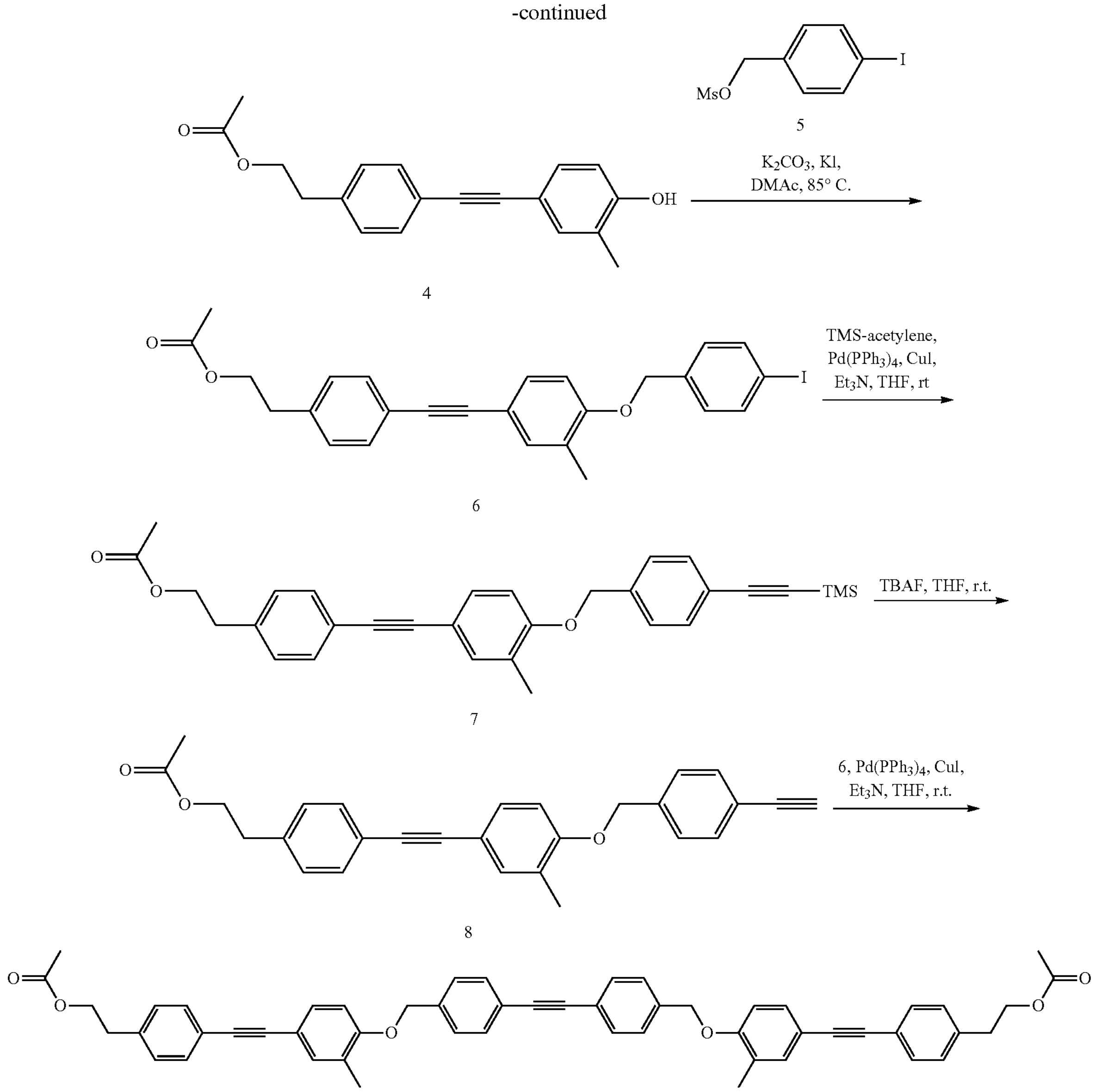

B-1

(1) Synthesis of Compound 2

The compound 1 (5.47 g, 35.5 mol) was dissolved in a mixed solution of tetrahydrofuran (THF) (30 mL) and pyridine (15 mL). The obtained solution was cooled in an ice water bath, acetic anhydride ($Ac_2O$) (5.44 g, 53.3 mmol) and 4-dimethylaminopyridine (DMAP) (0.43 g, 3.6 mmol) were added thereto, and stirring was carried out at room temperature (25° C.) for 3 hours. Ethyl acetate (50 mL) and water (50 mL) were added to the obtained solution, and then extraction was carried out with ethyl acetate. The obtained organic layer was washed with a saline solution and dried with magnesium sulfate. The organic layer was filtered, the solvent was distilled off under reduced pressure, and the obtained residue was purified by flash column chromatography, whereby a compound 2 (6.18 g, 32.8 mmol) was obtained. The yield was 92.4%.

(2) Synthesis of Compound 4

The compound 2 (1.54 g, 8.20 mmol) and the compound 3 (1.60 g, 6.84 mmol) were dissolved in THF (12.8 mL) in a nitrogen atmosphere, and triethylamine (6.92 g, 68.4 mmol) was added thereto. After nitrogen bubbling of the obtained solution for 20 minutes, tetrakis(triphenylphosphine)palladium (0) ($Pd(PPh_3)_4$) (0.40 g, 0.34 mmol) and CuI (0.13 g, 0.68 mmol) were added thereto, and the resultant mixture was stirred at room temperature for 1 hour. Ethyl acetate (30 mL) was added to the obtained solution, and the resultant mixture was filtered and sequentially washed with water, 1 mol/L hydrochloric acid, and then a saline solution. The obtained organic layer was dried with magnesium sulfate, and the organic layer was filtered. The solvent was distilled off under reduced pressure, and the obtained residue was purified by flash column chromatography, whereby a compound 4 (1.61 g, 5.47 mmol) was obtained. The yield was 80.0%.

(3) Synthesis of Compound 6

The compound 4 (0.70 g, 2.4 mmol) and the compound 5 (0.74 g, 2.4 mmol) were dissolved in dimethylacetamide (DMAc) (12 mL), potassium carbonate (0.39 g, 2.9 mmol)

and potassium iodide (0.039 g, 0.24 mmol) were added thereto, and the resultant mixture was stirred at 85° C. for 2 hours. The obtained solution was cooled to room temperature, ethyl acetate (70 mL) and water (30 mL) were added thereto, and then extraction was carried out with ethyl acetate. The obtained organic layer was sequentially washed with water and then a saline solution, followed by being dried with magnesium sulfate. After filtering the organic layer, the solvent was distilled off under reduced pressure, and the obtained residue was purified by flash column chromatography, whereby a compound 6 (0.82 g, 1.6 mmol) was obtained. The yield was 68%.

(4) Synthesis of Compound 8

The compound 6 (0.40 g, 0.78 mmol) was dissolved in THF (3.2 mL) in a nitrogen atmosphere, and triethylamine (0.79 g, 7.8 mmol) was added thereto. After nitrogen bubbling of the obtained solution for 20 minutes, trimethylsilyl acetylene (0.092 g, 0.94 mmol), $Pd(PPh_3)_4$ (0.045 g, 0.039 mmol) and CuI (0.010 g, 0.078 mmol) were added thereto, and the resultant mixture was stirred at room temperature for 1 hour. Ethyl acetate (30 mL) and water (10 mL) were added to the obtained solution, and then extraction was carried out with ethyl acetate. The obtained organic layer was washed with a saline solution and then dried with magnesium sulfate. After filtering the organic layer, the solvent was distilled off under reduced pressure, and the obtained residue was purified by flash column chromatography, whereby a compound 7 was obtained.

The obtained compound 7 was dissolved in THF (2.8 mL). The obtained solution was cooled in an ice water bath, a THF solution of tetra-n-butylammonium fluoride (TBAF) (1 mol/L, 0.86 mL, 0.86 mmol) was added thereto, and stirring was carried out at room temperature for 1 hour. The obtained solution was cooled in an ice water bath, ethyl acetate (30 mL) and water (10 mL) were added thereto, and then extraction was carried out with ethyl acetate. The obtained organic layer was washed with a saline solution and then dried with magnesium sulfate. After filtering the organic layer, the solvent was distilled off under reduced pressure, and the obtained residue was purified by flash column chromatography, whereby a compound 8 (0.32 g, 0.78 mmol) was obtained. The yield was 99.6%.

(5) Synthesis of Compound B-1

The compound 6 (0.37 g, 0.72 mmol) and the compound 8 (0.32 g, 0.78 mmol) were dissolved in THF (3.0 mL) in a nitrogen atmosphere, and triethylamine (0.73 g, 7.2 mmol) was added thereto. After nitrogen bubbling of the obtained solution for 20 minutes, $Pd(PPh_3)_4$ (0.042 g, 0.036 mmol) and CuI (0.014 g, 0.072 mmol) were added thereto, and the resultant mixture was stirred at room temperature for 1 hour. Chloroform (30 mL) was added to the obtained reaction solution, the solvent was distilled off under reduced pressure, and the obtained residue was purified by flash column chromatography to obtain the compound B-1 (0.22 g, 0.28 mmol). The yield was 39%.

$^1$H-NMR ($CDCl_3$): δ=2.04 (s, 6H), 2.29 (s, 6H), 2.94 (t, 4H), 4.28 (t, 4H), 5.12 (s, 4H), 6.79-6.85 (m, 2H), 7.19 (d, 4H), 7.30-7.37 (m, 4H), 7.39-7.48 (m, 8H), 7.56 (d, 4H)

Synthesis Example 2: Synthesis of Compound B-2

The compound B-1 was synthesized according to the following scheme.

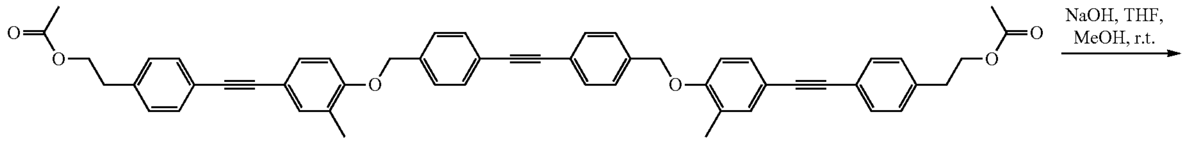

B-1

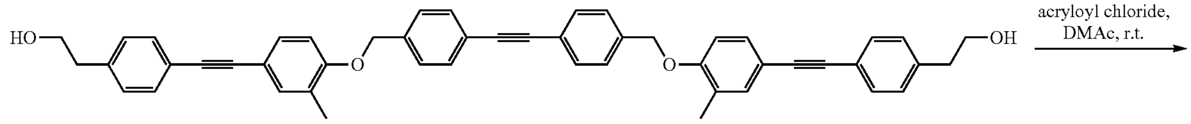

9

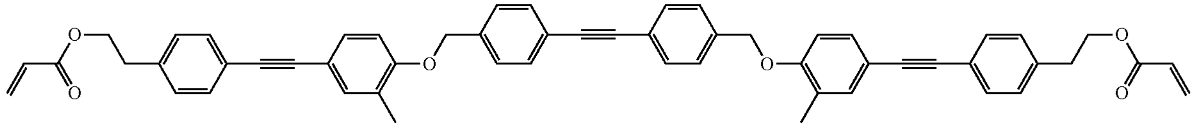

B-2

(6) Synthesis of Compound 9

The compound B-1 (0.22 g, 0.28 mmol) was dissolved in a mixed solution of THF (2 mL) and methanol (2 mL), a 1 mol/L aqueous NaOH solution (0.44 g, 0.42 mmol) was added thereto, and stirring was carried out for 4 hours. Water (10 mL) was added to the obtained solution, and extraction was carried out with chloroform. The obtained organic layer was dried with magnesium sulfate. The organic layer was filtered, the solvent was distilled off under reduced pressure, and the obtained residue was purified by flash column chromatography, whereby a compound 9 (0.19 g, 0.27 mmol) was obtained. The yield was 95%.

(7) Synthesis of Compound B-2

The compound 9 (0.19 g, 0.27 mmol) was dissolved in DMAc (3 mL). The obtained solution was cooled in an ice water bath, acryloyl chloride (0.086 g, 0.95 mmol) was added thereto, and stirring was carried out at room temperature for 1 hour. Chloroform (10 mL) and water (10 mL) were added to the obtained solution, and then extraction was carried out with chloroform. The obtained organic layer was washed with a saline solution and then dried with magnesium sulfate. After filtering the organic layer, the solvent was distilled off under reduced pressure, and the obtained residue was purified by flash column chromatography, whereby the compound B-2 (0.16 g, 0.20 mmol) was obtained. The yield was 72.8%.

$^1$H-NMR ($CDCl_3$): δ=2.29 (s, 6H), 2.99 (t, 4H), 4.38 (t, 4H), 5.12 (s, 4H), 5.81 (d, 2H), 6.10 (d, 2H), 6.38 (d, 2H), 6.79-6.85 (m, 2H), 7.20 (d, 4H), 7.31-7.38 (m, 4H), 7.40-7.49 (m, 8H), 7.57 (d, 4H)

Synthesis Example 3: Synthesis of Compound B-3

The compound B-3 was synthesized according to the following scheme. It is noted that a compound 10 was synthesized according to Chun, J. -H, et al. Org. Biomol. Chem. 11, 6300 (2013), and a compound 13 was synthesized according to WO2011/050276A. TBS indicates a tert-butyldimethylsilyl group.

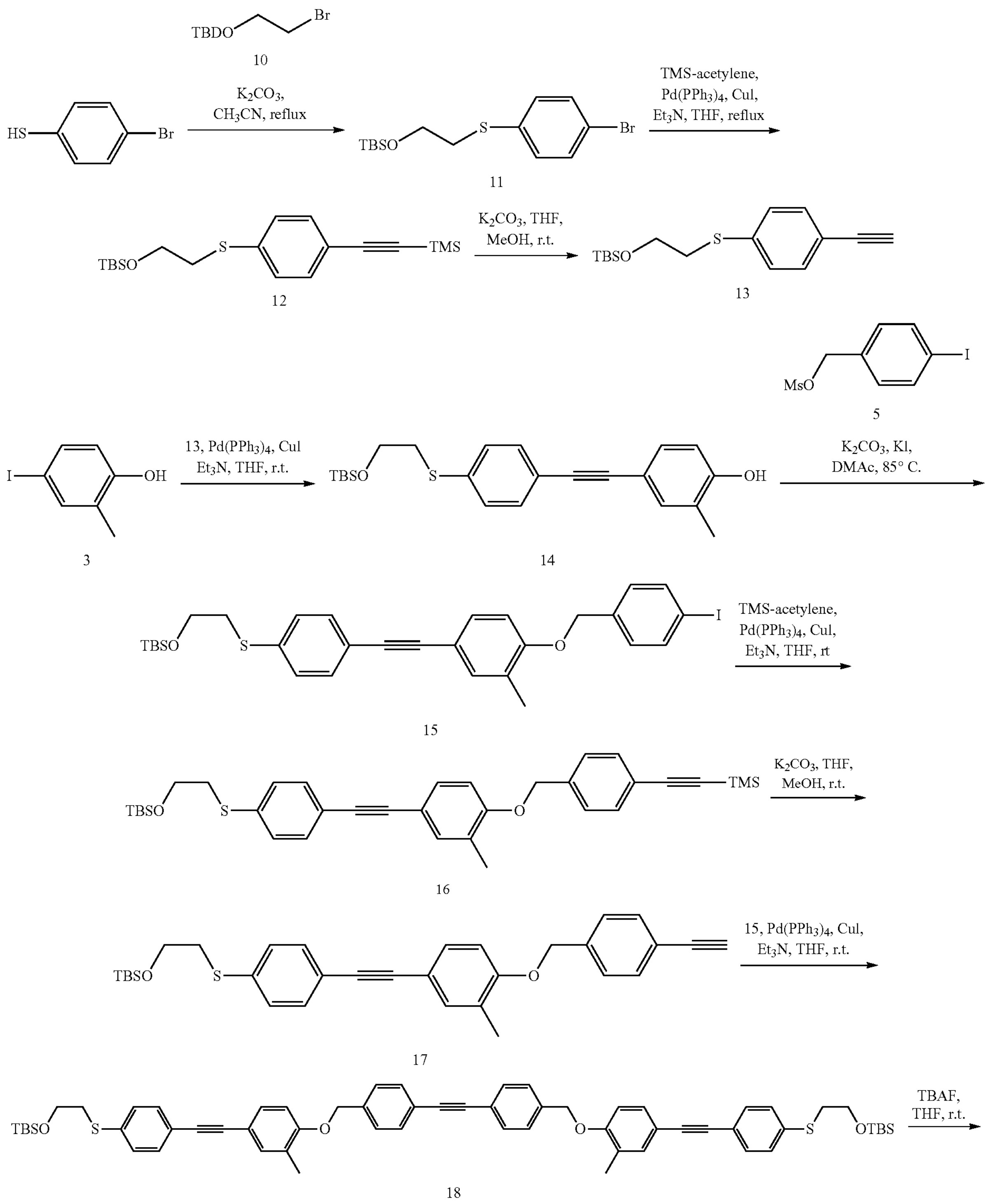

10

11

12

13

5

3

14

15

16

17

18

-continued

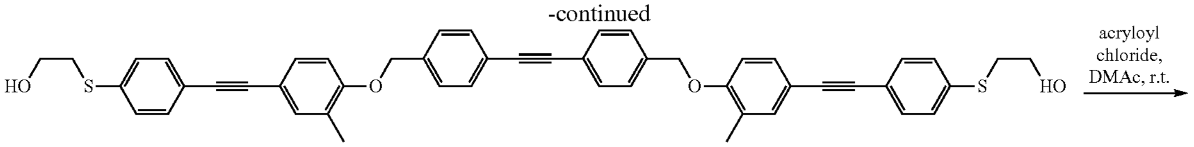

19

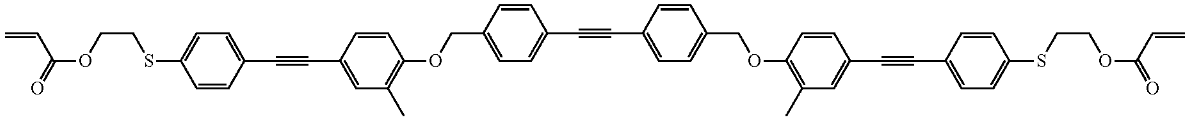

B-3

(8) Synthesis of Compound 14

A compound 14 was synthesized in the same manner as in the section of "(2) Synthesis of compound 4", except that the compound 13 was used instead of the compound 2 in the section of "(2) Synthesis of compound 4" described above.

(9) Synthesis of Compound 15

A compound 15 was synthesized in the same manner as in the section of "(3) Synthesis of compound 4", except that the compound 14 was used instead of the compound 4 in the section of "(3) Synthesis of compound 4" described above.

(10) Synthesis of Compound 16

A compound 16 was synthesized in the same manner as in the section of "(4) Synthesis of compound 8", except that in the synthesis of the compound 7 in the section of "(4) Synthesis of compound 8", the compound 15 was used instead of the compound 6.

(11) Synthesis of Compound 17

The compound 16 (1.58 g, 2.70 mmol) was dissolved in a mixed solution of THF (7.90 mL) and methanol (MeOH) (7.90 mL), potassium carbonate (1.12 g, 8.10 mmol) was added thereto, and the resultant mixture was stirred at room temperature for 1 hour. Water was added to the obtained solution, and then extraction was carried out with ethyl acetate. The obtained organic layer was washed with a saline solution and then dried with magnesium sulfate. After filtering the organic layer, the solvent was distilled off under reduced pressure, and the obtained residue was purified by flash column chromatography, whereby a compound 17 (1.15 g, 2.24 mmol) was obtained. The yield was 83.0%.

(12) Synthesis of Compound 18

A compound 18 was synthesized in the same manner as in the section of "(5) Synthesis of compound B-1", except that the compound 15 was used instead of the compound 6 and the compound 17 was used instead of the compound 8 in the section of "(5) Synthesis of compound B-1".

(13) Synthesis of Compound 19

The compound 18 (1.1 g, 1.05 mmol) was dissolved in THF (8 mL). The obtained solution was cooled in an ice water bath, a THF solution of TBAF (1 mol/L, 2.3 mL, 2.3 mmol) was added thereto, and stirring was carried out at room temperature for 1 hour. The obtained solution was cooled in an ice water bath, chloroform (50 mL) and water (20 mL) were added thereto, and then extraction was carried out with chloroform. The obtained organic layer was washed with a saline solution and then dried with magnesium sulfate. After filtering the organic layer, the solvent was distilled off under reduced pressure, and the obtained residue was purified by flash column chromatography, whereby a compound 19 (0.70 g, 0.91 mmol) was obtained. The yield was 82%.

(14) Synthesis of Compound B-3

A compound B-3 was synthesized in the same manner as in (7), except that the compound 19 was used instead of the compound 9 in the synthesis (7) of the compound B-2.

$^1$H-NMR ($CDCl_3$): δ=2.29 (s, 6H), 3.22 (t, 4H), 4.35 (t, 4H), 5.12 (s, 4H), 5.85 (d, 2H), 6.10 (d, 2H), 6.40 (d, 2H), 6.79-6.85 (m, 2H), 7.20 (d, 4H), 7.31-7.38 (m, 4H), 7.40-7.49 (m, 8H), 7.57 (d, 4H)

Synthesis Example 4: Synthesis of Compound B-4

(15) Synthesis of Compound B-4

A compound B-4 was synthesized in the same manner, except that 2-methoxycarbonyl-4-iodophenol was used instead of the compound 3 (4-iodo-2-methylphenol) in the synthesis of the compound B-3.

$^1$H-NMR ($CDCl_3$): δ=3.22 (t, 4H), 3.93 (s, 6H), 4.35 (t, 4H), 5.22 (s, 4H), 5.85 (d, 2H), 6.09 (d, 2H), 6.39 (d, 2H), 6.95-6.70 (m, 2H), 7.20 (d, 4H), 7.30-7.48 (m, 8H), 7.30-7.48 (m, 6H), 8.01 (d, 2H)

B-1

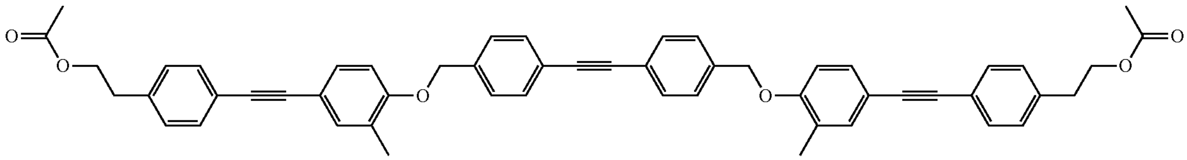

B-2

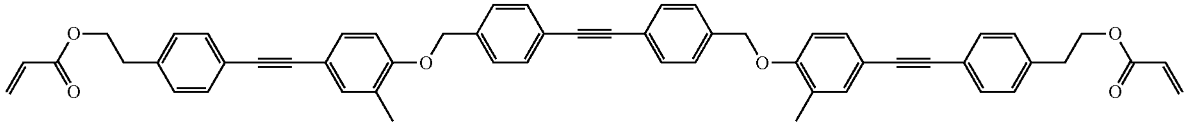

-continued

B-3

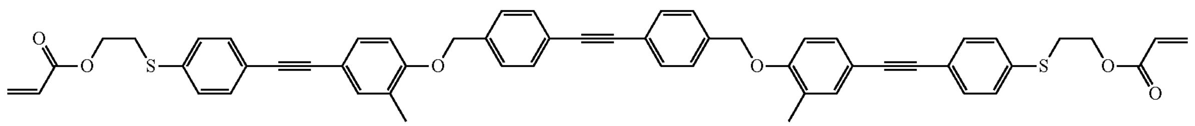

B-4

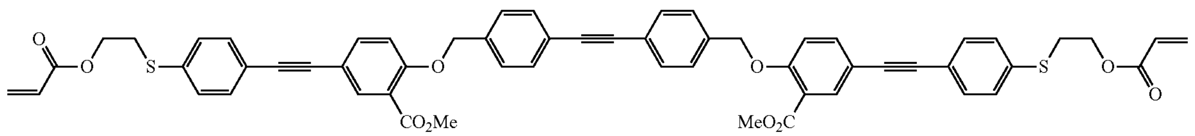

Examples 1 to 5 and Comparative Example 1

The following evaluations were carried out using the compounds B-1 to B-4 in Examples 1 to 5 and using the compound A-2 in Comparative Example 1.

<Evaluation of Liquid Crystallinity>

The liquid crystallinity of the compounds B-1 to B-4 and the compound A-2 was evaluated.

Each compound was heated on a hot stage and observed with a polarization microscope, and the phase transition temperature was measured to evaluate the presence or absence of liquid crystallinity. A case of having liquid crystallinity was evaluated as A, and a case of having no liquid crystallinity was evaluated as B. The results are shown in the column of "Liquid crystallinity" of "Compound 2" in Table 1.

<Evaluation of Solubility>

The solubility of the compounds B-1 to B-4 and the compound A-2 in cyclopentanone was evaluated.

Using cyclopentanone as a solvent, a solution in which each compound was ultrasonically dissolved or dissolved by heating was prepared, and then it was observed at room temperature (25° C.) whether or not the compound was precipitated in the solution. Solutions were prepared at various concentrations for each compound, the concentration at which the precipitation of the compound occurred was defined as the precipitation concentration, the solubility in a case where the precipitation concentration was more than 5% by mass was evaluated as A, and the solubility in a case where the precipitation concentration was 5% by mass or less was evaluated as B. The results are shown in the column of "Solubility" of "Compound 2" in Table 1.

<Evaluation of Durability>

As shown below, the durability of the optically anisotropic layer produced using the composition containing each of the compounds B-1 to B-4 and the compound A-2 was evaluated.

(Production of Optically Anisotropic Layer for Durability Test)

A coating liquid for a durability test having the following composition was prepared and applied by spin-coating onto a rubbing-treated glass attached with an alignment film. Each coating liquid for a durability test was irradiated with ultraviolet rays of 300 mJ/cm$^2$ through a filter that cuts light having a wavelength of 350 nm or less on a hot plate which had been heated to a temperature at which a nematic phase is shown, whereby an optically anisotropic film for a durability test was produced.

| Composition of coating liquid for durability test | |
|---|---|
| Compound 2 shown in Table 1 below | parts by mass shown in Table 1 below |
| Compound 1 shown in Table 1 below | parts by mass shown in Table 1 below |
| A polymerization initiator (IRGACURE (registered trade name) 907, manufactured by BASF SE) | 2 parts by mass |
| The following leveling agent T-1 | 0.1 parts by mass |
| Chloroform | 1,940 parts by mass |

As the compound 1, the above-described compound A-1 was used.

T-1

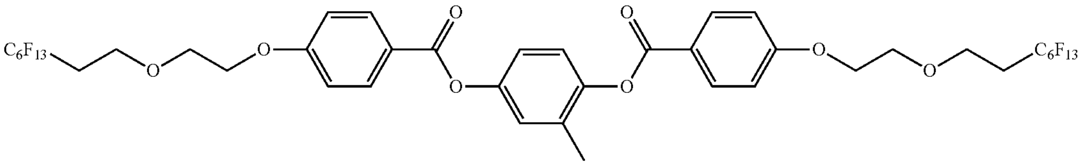

The produced optically anisotropic layer for durability test was allowed to be left for 136 hours at 100° C. and a humidity of 95%, whereby a moisture-heat resistance test was carried out. The Re before and after the durability test was measured, the durability in a case where the rate of change in Re shown below was less than 10% was evaluated as A, and the durability in a case where the rate of change in Re shown below was 10% or more was evaluated as B. The smaller the rate of change in Re, the more excellent the durability. The results are shown in the column of "Durability" of "Optically anisotropic layer" in Table 1.

It is noted that Re is the in-plane retardation.

$$\text{Rate of change in Re(\%)}=[100\times\{|(\text{Re before durability test})-(\text{Re after durability test})|\}/(\text{Re before durability test})]$$

Re at a wavelength of 550 nm was measured using Axoscan (manufactured by Axometrics Inc.), and the film thickness is measured using a scanning electron microscope (SEM). The measurement temperature was room temperature (25° C.).

Preparation of Compositions E (E-1 to E-6)

A composition E to be used in the evaluation of liquid crystallinity, the evaluation of Iso point, and the evaluation of refractive index anisotropy Δn of the composition described later, and in the production of an optical element was prepared. Specifically, as the composition E, compositions E-1 to E-6 shown in Table 1 below were prepared.

| Composition E | |
|---|---|
| Compound 2 shown in Table 1 below | parts by mass shown in Table 1 below |
| Compound 1 shown in Table 1 below | parts by mass shown in Table 1 below |
| A polymerization initiator (IRGACURE (registered trade name) 907, manufactured by BASF SE) | 3.00 parts by mass |
| The above leveling agent T-1 | 0.08 parts by mass |
| Methyl ethyl ketone | 927.7 parts by mass |

As the compound 1, the above-described compound A-1 was used.

<Evaluation of Liquid Crystallinity of Composition>

The liquid crystallinity of the compositions E-1 to E-6 respectively containing the compounds B-1 to B-4, and the compound A-2 was evaluated.

Each composition was heated on a hot stage and observed with a polarization microscope, and the phase transition temperature was measured to evaluate the presence or absence of liquid crystallinity. A case of having liquid crystallinity was evaluated as A, and a case of having no liquid crystallinity was evaluated as B. The results are shown in the column of "Liquid crystallinity of composition" in Table 1.

<Evaluation of Iso Point>

As shown below, the Iso point of the optically anisotropic layer produced using each of the compositions E-1 to E-6 respectively containing the compounds B-1 to B-4 and the compound A-2 was evaluated.

The composition E was heated on a hot stage and observed with a polarization microscope, the phase transition temperature was measured, and the Iso point temperature was measured. The following evaluation value was determined based on the obtained temperature. The results are shown in the column of "Iso point" in Table 1.

A: 175° C.≤Iso point

B: 155° C.≤Iso point<175° C.

C: Iso point<155° C.

<Evaluation of Refractive Index Anisotropy Δn>

As shown below, the refractive index anisotropy Δn of the optically anisotropic layer produced using each of the compositions E-1 to E-6 respectively containing the compounds B-1 to B-4 and the compound A-2 was evaluated.

As the refractive index anisotropy Δn, a refractive index difference Δn550 at a wavelength of 550 nm was evaluated. The refractive index difference Δn550 in refractive index refers to a value obtained by applying the liquid crystal composition (the composition E) onto a support with an alignment film for retardation measurement which is prepared separately, aligning the director (optical axis) of the liquid crystal compound to be parallel to the surface of the support, irradiating the liquid crystal compound with ultraviolet light for immobilization to obtain a liquid crystal immobilized layer (cured layer), measuring the retardation value and the film thickness of the liquid crystal immobilized layer, and carrying out the calculation. It is noted that Δn550 can be calculated by dividing the retardation value by the film thickness.

The retardation value at a wavelength of 550 nm was measured using Axoscan (manufactured by Axometrics Inc.), and the film thickness is measured using a scanning electron microscope (SEM). The measurement temperature was 80° C.

For the composition E, a refractive index difference Δn550 was measured. The obtained Δn550 was evaluated according to the following standards. The results are shown in the column of "Refractive index difference Δn550" of "Optically anisotropic layer" in Table 1.

A: 0.325≤Δn550

B: 0.300≤Δn550<0.325

C: 0.250≤Δn550<0.300

D: Δn550<0.250

[Production of Optical Element]

<Preparation of Support and Saponification Treatment of Support>

As a support, a commercially available triacetyl cellulose film "Z-TAC" (manufactured by Fujifilm Corporation) was used.

The support was allowed to pass through a dielectric heating roll at a temperature of 60° C. so that the surface temperature of the support was increased to 40° C.

Next, the following alkali solution was applied onto a single surface of the support using a bar coater in a coating amount of 14 mL (liter)/$m^2$, the support was heated to 110° C., and the support was transported for 10 seconds under a steam-type far infrared heater (manufactured by Noritake Co., Ltd.).

Subsequently, 3 mL/$m^2$ of pure water was applied onto the surface of the support, onto which the alkali solution had been applied, using the same bar coater. Next, water cleaning using a foundry coater and water draining using an air knife were repeated three times, and then the support was transported and dried in a drying zone at 70° C. for 10 seconds, whereby the surface of the support was subjected to the alkali saponification treatment.

| Alkali solution | |
|---|---|
| Potassium hydroxide | 4.70 parts by mass |
| Water | 15.80 parts by mass |
| Isopropyl alcohol | 63.70 parts by mass |
| A surfactant SF-1: $C_{14}H_{29}O(CH_2CH_2O)_2OH$ | 1.0 part by mass |
| Propylene glycol | 14.8 parts by mass |

<Formation of Undercoat Layer>

The following coating liquid for forming an undercoat layer was continuously applied onto the surface of the support, which had been subjected to the alkali saponification treatment, using a #8 wire bar. The support on which the coating film had been formed was dried using hot air at 60° C. for 60 seconds and further dried using hot air at 100° C. for 120 seconds to form an undercoat layer.

| Coating liquid for forming undercoat layer | |
|---|---|
| The following modified polyvinyl alcohol | 2.40 parts by mass |
| Isopropyl alcohol | 1.60 parts by mass |

-continued

| Coating liquid for forming undercoat layer | |
|---|---|
| Methanol | 36.00 parts by mass |
| Water | 60.00 parts by mass |

Modified polyvinyl alcohol (the ratios of repeating units in the following structural formula is in terms of mass ratio)

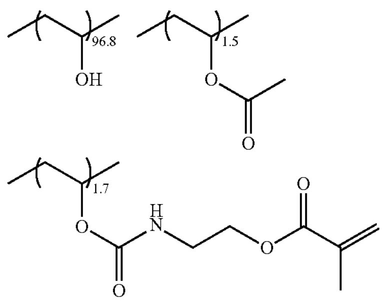

<Formation of Alignment Film>

The following coating liquid for forming an alignment film was continuously applied onto the support, onto which the undercoat layer had been formed, using a #2 wire bar. The support on which the coating film of the coating liquid for forming an alignment film had been formed was dried using a hot plate at 60° C. for 60 seconds to form an alignment film.

| Coating liquid for forming alignment film | |
|---|---|
| The following material D for photo alignment | 1.00 part by mass |
| Water | 16.00 parts by mass |
| Butoxyethanol | 42.00 parts by mass |
| Propylene glycol monomethyl ether | 42.00 parts by mass |

Material D for Photo Alignment

D

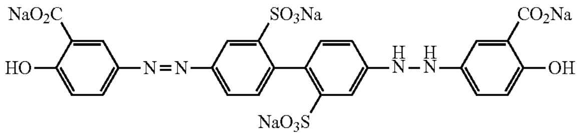

<Exposure of Alignment Film>

The alignment film was exposed using the exposure device of FIG. 5 of WO2020/22496A to form an alignment film P-1 having an alignment pattern.

In the exposure device, a laser that emits a laser beam having a wavelength of 325 nm was used as the laser. The exposure amount of the interference light was 2,000 mJ/cm$^2$. It is noted that one period (the length over which the optical axis derived from the liquid crystal compound rotates 180°) of an alignment pattern formed by interference of two laser beams was controlled by changing the intersecting angle (the intersecting angle β) between the two beams.

<Formation of Optically Anisotropic Layer>

As a composition for forming an optically anisotropic layer, the above-described composition E was used.

The optically anisotropic layer was formed by subjecting the alignment film P-1 multilayer coating with the composition E.

The multilayer coating refers to repeating a procedure in which, first, the composition is applied for a first layer on the alignment film P-1, heated, and cooled, followed by being cured with ultraviolet rays to produce a liquid crystal immobilized layer, and then, for a second layer and subsequent layers, this liquid crystal immobilized layer is subjected to multiple coating by the application of the composition E-1, heating, and cooling, followed by curing with ultraviolet rays in the same manner.

Due to the formation by the multilayer coating, the alignment direction of the alignment film is reflected over the upper surface of the liquid crystal layer from the lower surface (the surface on the alignment film P-1 side) even in a case where the film thickness of the liquid crystal layer is increased.

First, the following composition E was applied for the first liquid crystal layer onto the alignment film P-1 to form a coating film, the coating film was heated to 120° C. using a hot plate and then cooled to 60° C., followed by being irradiated with ultraviolet rays having a wavelength of 365 nm at an irradiation dose of 2,000 mJ/cm$^2$ using a high-pressure mercury lamp in a nitrogen atmosphere, whereby the alignment of the liquid crystal compound was fixed. At this time, the film thickness of the first liquid crystal layer was 0.3 μm.

For the second and subsequent liquid crystal layers, this liquid crystal layer was subjected to multiple coating, heating, and cooling under the same conditions as described above, followed by curing with ultraviolet rays to produce a liquid crystal immobilized layer (a cured layer).

In this way, the multiple coating was repeated such that the refractive index anisotropy Δn×film thickness was 325 nm, and an optically anisotropic layer was formed to produce an optical element.

TABLE 1

| | Composition | | | | | | | | | Optically anisotropic layer | |
|---|---|---|---|---|---|---|---|---|---|---|---|
| | | Compound 1 | | Compound 2 | | | | Liquid crystallinity of composition | | | |
| | Kind | Kind | Content (part by mass) | Kind | Liquid crystallinity | Solubility | Content (part by mass) | | Iso point | Durability | Refractive index difference Δn550 |
| Comparative Example 1 | E-1 | A-1 | 90 | A-2 | A | A | 10 | A | C | A | D |
| Example 1 | E-2 | A-1 | 80 | B-1 | A | B | 20 | A | B | B | C |
| Example 2 | E-3 | A-1 | 80 | B-2 | A | B | 20 | A | B | A | C |
| Example 3 | E-4 | A-1 | 80 | B-3 | A | B | 20 | A | B | A | B |

TABLE 1-continued

| | Composition | | | | | | | | | | |
|---|---|---|---|---|---|---|---|---|---|---|---|
| | | Compound 1 | | Compound 2 | | | | Liquid | Optically anisotropic layer | | |
| | Kind | Kind | Content (part by mass) | Kind | Liquid crystallinity | Solubility | Content (part by mass) | crystallinity of composition | Iso point | Durability | Refractive index difference Δn550 |
| Example 4 | E-5 | A-1 | 80 | B-4 | A | A | 20 | A | B | A | B |
| Example 5 | E-6 | A-1 | 50 | B-4 | A | A | 50 | A | A | A | A |

The compound A-2 used as the compound 2 in Comparative Example 1 is a mixture obtained by carrying out mixing the following a-2-1/a-2-2/a-2-3 compounds at a ratio of 84/14/2 (in terms of mass ratio).

A-2 a-2-1

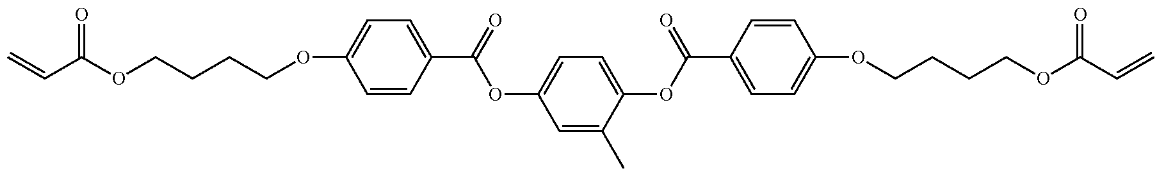

a-2-2

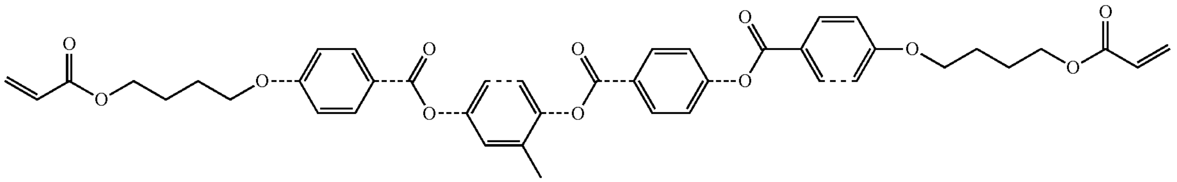

a-2-3

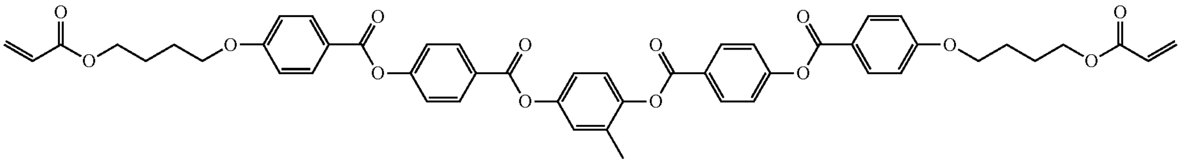

<Measurement of Diffraction Efficiency>

An evaluation optical system in which a light source for evaluation, a polarizer, a ¼ wavelength plate, the optical element of Example 5, and a screen were arranged in this order was prepared. A laser pointer having a wavelength of 650 nm was used as the light source for evaluation, and SAQWP05M-700 manufactured by Thorlabs Inc. was used as the ¼ wavelength plate. The slow axis of the ¼ wavelength plate was arranged at a relationship of 45° with respect to the absorption axis of the polarizer. In addition, the optical element of Example 5 was arranged so that the support surface faced the light source side.

As a result of causing the light transmitted from the light source for evaluation through the polarizer and the ¼ wavelength plate, to be incident on the optical element of Example 5 with being perpendicular to the film surface, a part of the light transmitted through the optical element was diffracted, and a plurality of bright spots could be confirmed on the screen.

The intensity of the diffracted light corresponding to each of the bright spots on the screen and the intensity of the zero-order light w measured with a power meter, and the diffraction efficiency was calculated according to the following expression.

Diffraction efficiency=(intensity of first-order light)/(intensity of zero-order light+intensity of diffracted light other than first-order light)

The obtained diffraction efficiency was as high as 99% or more.

Using a polarization microscope, it was confirmed that the optically anisotropic layer of this example had a periodic alignment surface as shown in FIG. 3 of WO2020/22496A. In the alignment pattern of the optically anisotropic layer, the one period Λ over which the optical axis derived from the liquid crystal compounds (compound B-4 and compound A-1) rotated 180° was 1.0 μm. The period Λ was determined by measuring the period of the bright and dark pattern observed under the crossed nicol condition using a polarization microscope.

From the results shown in Table 1, it was found that the liquid crystal composition obtained by blending the compound represented by General Formula (I) has a high Iso point, and the optically anisotropic layer obtained by curing the liquid crystal composition has a high refractive index anisotropy Δn (refractive index difference Δn550) (Examples 1 to 5).

In particular, from the comparison between Examples 4 and 5, it was found that in a case of increasing the blending amount of the compound represented by General Formula (I), the Iso point of the liquid crystal composition can be further improved, and thus the refractive index anisotropy Δn (refractive index difference Δn550) of the cured optically anisotropic layer obtained by curing the liquid crystal composition is further increased.

In addition, as described above, in a case where the optical element produced by using the composition containing the compound represented by General Formula (I) was used, a high diffraction efficiency could be obtained.

On the other hand, it was found that the liquid crystal composition which does not contain the compound represented by General Formula (I) has an Iso point of lower than 155° C., and the refractive index anisotropy Δn (refractive index difference Δn550) of the optically anisotropic layer obtained by curing the liquid crystal composition is low as compared with Examples 1 to 5 (Comparative Example 1).

Example 6

As Example 6, a light guide element was produced using a composition containing the liquid crystal compound B-4, the polymerizable liquid crystal compound A-1, and a chiral agent, as shown below.

The following composition E-7 was prepared as a composition for forming a cholesteric liquid crystal layer as shown in FIG. 6 of WO2020/22496A. In the structural formula of the following chiral agent Ch-2, Bu represents an n-butyl group.

| Composition E-7 | | |
|---|---|---|
| Liquid crystal compound B-4 | 50.00 | parts by mass |
| Polymerizable liquid crystal compound A-1 | 50.00 | parts by mass |
| The following polymerization initiator PI-1 | 3.00 | parts by mass |
| The following chiral agent Ch-1 | 4.40 | parts by mass |
| The following chiral agent Ch-2 | 1.00 | part by mass |
| Methyl ethyl ketone | 201.31 | parts by mass |

PI-1
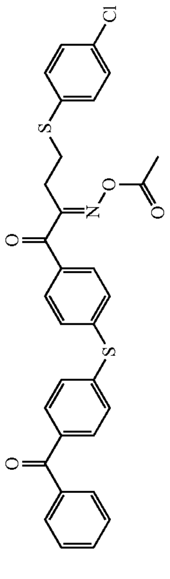
Ch-1
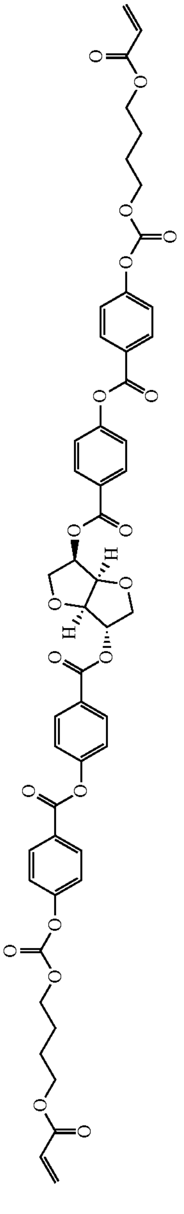
Ch-2
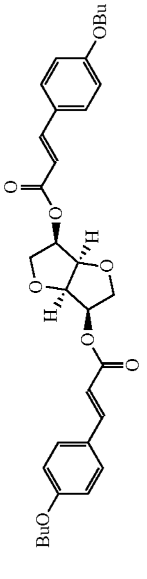

The alignment film P-1 was produced in the same manner as in the above-described <Preparation of support and saponification treatment of support>, <Formation of undercoat layer>, <Formation of alignment film>, and <Exposure of alignment film> in [Production of optical element].

A cholesteric liquid crystal layer was formed by subjecting the alignment film P-1 to multilayer coating with the composition E-7 until the film thickness became 3.5 μm. The multilayer coating refers to repeating a procedure in which, first, the composition E-7 is applied for a first layer on an alignment film and heated, followed by being cured with ultraviolet rays to produce a liquid crystal immobilized layer, and then, for a second layer and subsequent layers, this liquid crystal immobilized layer is subjected to multiple coating by the application of the composition A-1 and heating and curing with ultraviolet rays in the same manner. Due to the formation by the multilayer coating, the alignment direction of the alignment film is reflected over the upper surface of the liquid crystal layer from the lower surface even in a case where the total thickness of the liquid crystal layer is increased.

As the optically anisotropic layer for the first layer, the composition E-7 was applied onto the alignment film P-1 at 1,000 rotations per minute (rpm) using a spin coater. The coating film was heated on a hot plate at 80° C. for 3 minutes and then irradiated at 50° C. with ultraviolet rays having a wavelength of 365 nm at an irradiation dose of 300 $mJ/cm^2$ using a high-pressure mercury lamp in a nitrogen atmosphere whereby the alignment of the liquid crystal compound was fixed.

This liquid crystal layer was subjected to multiple coating for the second and subsequent liquid crystal layers, followed by heating and then curing with an ultraviolet ray under the same conditions as described above to form a cholesteric liquid crystal layer.

The formed cholesteric liquid crystal layer was bonded to a light guide plate (a glass having a refractive index of 1.80 and a thickness of 0.50 mm), and light of 532 nm was allowed to be incident from the light guide plate side in the normal direction. As a result of the above, it was confirmed that the incident light was reflected in the cholesteric liquid crystal layer beyond the critical angle in a direction different from the specular reflection direction and guided in the light guide plate.

According to the present invention, it is possible to provide a compound having a high refractive index anisotropy Δn, a composition, a cured product, an optically anisotropic body, an optical element, and a light guide element, containing the compound, each of which contains the compound.

The present invention has been described in detail and with reference to specific embodiments; however, it is apparent to those skilled in the art that various changes and modifications can be made without departing from the spirit and the scope of the invention.

What is claimed is:

1. A compound represented by General Formula (I), (I)

$$P^1—S^1—A^1—\equiv—A^2\text{-}\!\left(Z—A^3—\equiv—A^4\right)_{m1}\!—S^2—P^2$$

in the General Formula (I), $P^1$ and $P^2$ each independently represent a polymerizable group represented by any one of Formulae (P-1) to (P-19):

(P-1)

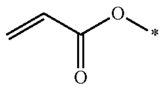

(P-2)

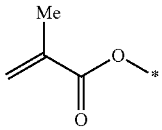

(P-3)

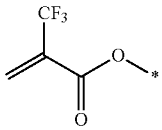

(P-4)

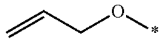

(P-5)

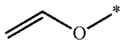

(P-6)

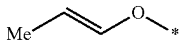

(P-7)

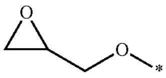

(P-8)

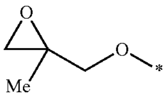

(P-9)

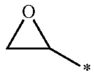

(P-10)

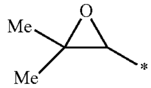

(P-11)

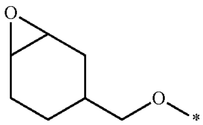

(P-12)

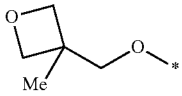

(P-13)

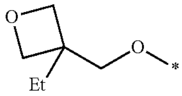

(P-14)

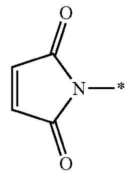

-continued (P-15)

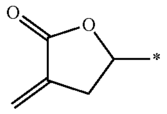

(P-16)

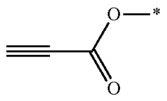

(P-17)

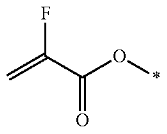

(P-18)

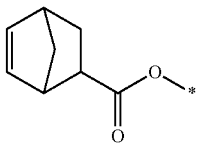

(P-19)

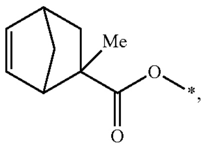

$S^1$ and $S^2$ each independently represent a single bond or a divalent linking group, $A^1$ to $A^4$ each independently represent a non-aromatic ring group, an aromatic hydrocarbon ring group, or an aromatic heterocyclic group, which may have a substituent, a plurality of $A^3$'s and a plurality of $A^4$'s may be the same or different from each other, Z represents —O—, —S—, —CHRCHR—, —OCHR—, —CHRO—, —CO—, —SO—, —$SO_2$—, —COO—, —OCO—, —CO—S—, —S—CO—, —O—CO—O—, —SCHR—, —CHRS—, —SO—CHR—, —CHR—SO—, —$SO_2$—CHR—, —CHR—$SO_2$—, —$CF_2O$—, —$OCF_2$—, —$CF_2S$—, —$SCF_2$—, —OCHRCHRO—, —SCHRCHRS—, —SO—CHRCHR—SO—, —$SO_2$—CHRCHR—$SO_2$—, —CH═CH—COO—, —CH═CH—OCO—, —COO—CH═CH—, —OCO—CH═CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR═CR—, —CR═N—, —N═CR—, —N═N—, —CR═N—N═CR—, —CF═CF—, or a single bond, R represents a hydrogen atom or an alkyl group having 1 to 10 carbon atoms, a plurality of Z's may be the same or different from each other, in a case where a plurality of R's is present, the plurality of R's may be the same or different from each other, and m1 represents an integer of 2 to 7.

2. The compound according to claim 1, wherein m1 in the General Formula (I) represents 2.

3. The compound according to claim 1, wherein at least one of $A^1$, . . . , or $A^4$ in the General Formula (I) has at least one substituent selected from the group consisting of an alkyl group having 1 to 20 carbon atoms, an alkoxy group having 1 to 20 carbon atoms, an alkylamino group having 1 to 20 carbon atoms, an alkylthio group having 1 to 20 carbon atoms, an alkanoyl group having 1 to 20 carbon atoms, an alkanoyloxy group having 1 to 20 carbon atoms, an alkanoylamino group having 1 to 20 carbon atoms, an alkanoylthio group having 1 to 20 carbon atoms, an alkyloxycarbonyl group having 2 to 20 carbon atoms, an alkylaminocarbonyl group having 2 to 20 carbon atoms, an alkylthiocarbonyl group having 2 to 20 carbon atoms, a hydroxy group, an amino group, a mercapto group, a carboxy group, a sulfo group, an amide group, a cyano group, a nitro group, a halogen atom, and a polymerizable group, provided that in a case where the substituent has —$CH_2$—, at least one —$CH_2$— contained in the substituent may be replaced with —O—, —CO—, —CH═CH—, or —C≡C—, and in a case where the substituent has a hydrogen atom, at least one hydrogen atom contained in the substituent may be replaced with a fluorine atom.

4. The compound according to claim 1, wherein in the General Formula (I), $S^1$ represents a group represented by General Formula (II), and $S^2$ represents a group represented by General Formula (III), $$*\text{—S—}W^1\text{—}* \quad \text{(II)}$$

$$*\text{—S—}W^2\text{—}** \quad \text{(III)}$$

in the General Formulae (II) and (III), $W^1$ and $W^2$ each independently represent an alkylene group having 1 to 15 carbon atoms, where one or more methylene groups contained in the alkylene group may be each independently replaced with —O—, —S—, or —CO—,

*'s each represent a bonding position to $A^1$ or $A^4$, which is directly linked to $S^1$ or $S^2$, and

**'s each represent a bonding position to $P^1$ or $P^2$.

5. The compound according to claim 1, wherein Z in the General Formula (I) represents —CHRCHR—, —OCHR—, or —CHRO—, provided that R represents a hydrogen atom or an alkyl group having 1 to 10 carbon atoms, and in a case where a plurality of R's is present, the plurality of R's may be the same or different from each other.

6. The compound according to claim 1, wherein the compound represented by the General Formula (I) is a compound represented by General Formula (I-2), (I-2)

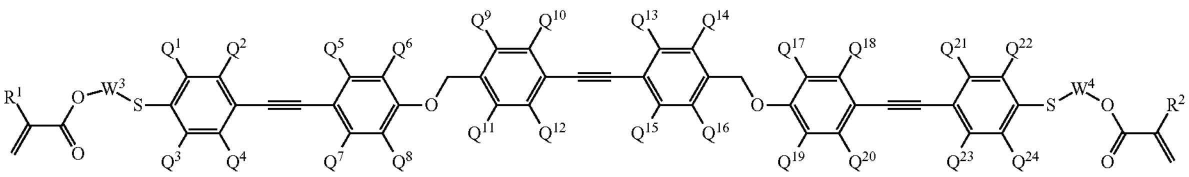

in the General Formula (I-2), $R^1$ and $R^2$ each independently represent a hydrogen atom or a methyl group, $W^3$ and $W^4$ each independently represent an alkylene group having 1 to 6 carbon atoms, and $Q^1$ to $Q^{24}$ each independently represent a hydrogen atom, a fluorine atom, a chlorine atom, a nitro group, a cyano group, an alkyl group having 1 to 20 carbon atoms, an alkyloxycarbonyl group having 2 to 20 carbon atoms, or an alkylaminocarbonyl group having 2 to 20 carbon atoms.

7. The compound according to claim 1, wherein the compound has liquid crystallinity.

8. A composition comprising:

the compound according to claim 1.

9. The composition according to claim 8, further comprising:

a polymerization initiator.

10. The composition according to claim 8, further comprising:

a chiral agent.

11. The composition according to claim 8, wherein the composition has liquid crystallinity.

12. The composition according to claim 8, wherein the composition is used for forming an optically anisotropic layer.

13. A cured product that is obtained by curing the composition according to claim 8.

14. An optically anisotropic body that is obtained by curing the composition according to claim 8.

15. An optical element comprising:

an optically anisotropic layer formed from the composition according to claim 8, wherein the optically anisotropic layer has an alignment pattern, and the alignment pattern is an alignment pattern in which an orientation of an optical axis, derived from a compound contained in the composition, continuously changes rotationally along at least one in-plane direction.

16. A light guide element comprising:

the optical element according to claim 15; and a light guide plate.

17. A compound represented by General Formula (I), (I)

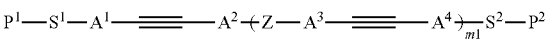

in the General Formula (I), $P^1$ and $P^2$ each independently represent a hydrogen atom or a substituent, $S^1$ and $S^2$ each independently represent a single bond or a divalent linking group, $A^1$ to $A^4$ each independently represent a non-aromatic ring group, an aromatic hydrocarbon ring group, or an aromatic heterocyclic group, which may have a substituent, a plurality of $A^3$'s and a plurality of $A^4$'s may be the same or different from each other, Z represents —CHRCHR—, —OCHR—, or —CHRO—, R represents a hydrogen atom or an alkyl group having 1 to 10 carbon atoms, a plurality of Z's may be the same or different from each other, in a case where a plurality of R's is present, the plurality of R's may be the same or different from each other, and m1 represents an integer of 2 to 7.

* * * * *